US008883836B2

(12) United States Patent
Cooper et al.

(10) Patent No.: US 8,883,836 B2
(45) Date of Patent: *Nov. 11, 2014

(54) SOLID FORMS OF BENDAMUSTINE HYDROCHLORIDE

(71) Applicant: Cephalon, Inc., Frazer, PA (US)

(72) Inventors: Martin Ian Cooper, Cambridge (GB); Laurent D. Courvoisier, Thorndale, PA (US); Mark Eddleston, Nottingham (GB); Robert E. McKean, Chester Springs, PA (US)

(73) Assignee: Cephalon, Inc., Frazer, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/200,738

(22) Filed: Mar. 7, 2014

(65) Prior Publication Data

US 2014/0187598 A1 Jul. 3, 2014

Related U.S. Application Data

(63) Continuation of application No. 13/874,575, filed on May 1, 2013, now Pat. No. 8,669,279, which is a continuation of application No. 13/301,979, filed on Nov. 22, 2011, now Pat. No. 8,445,524, which is a continuation of application No. 12/411,929, filed on Mar. 26, 2009, now abandoned.

(60) Provisional application No. 61/039,752, filed on Mar. 26, 2008.

(51) Int. Cl.
*C07D 235/16* (2006.01)

(52) U.S. Cl.
CPC .................................. *C07D 235/16* (2013.01)
USPC ........................................ 514/394; 548/310.1

(58) Field of Classification Search
CPC ....... A61K 31/4184; A61K 9/14; A61K 9/19; C07D 235/16
See application file for complete search history.

(56) References Cited

U.S. PATENT DOCUMENTS

| 4,670,262 | A | 6/1987 | Battelli et al. |
| 5,204,335 | A | 4/1993 | Sauerbier et al. |
| 5,227,373 | A | 7/1993 | Alexander et al. |
| 5,750,131 | A | 5/1998 | Wichert et al. |
| 5,770,230 | A | 6/1998 | Teagarden et al. |
| 5,776,456 | A | 7/1998 | Anderson et al. |
| 5,955,504 | A | 9/1999 | Wechter et al. |
| 5,972,912 | A | 10/1999 | Marek et al. |
| 6,034,256 | A | 3/2000 | Carter et al. |
| 6,077,850 | A | 6/2000 | Carter et al. |
| 6,090,365 | A | 7/2000 | Kaminski et al. |
| 6,271,253 | B1 | 8/2001 | Carter et al. |
| 6,380,210 | B1 | 4/2002 | Desimone et al. |
| 6,492,390 | B2 | 12/2002 | Carter et al. |
| 6,545,034 | B1 | 4/2003 | Carson et al. |
| 6,569,402 | B1 | 5/2003 | Cheesman et al. |
| 6,573,292 | B1 | 6/2003 | Nardella |
| 6,613,927 | B1 | 9/2003 | Kwok |
| 8,445,524 | B2 | 5/2013 | Courvoisier et al. |
| 2002/0102215 | A1 | 8/2002 | Klaveness et al. |
| 2003/0232874 | A1 | 12/2003 | Nardella |
| 2004/0053972 | A1 | 3/2004 | Nara |
| 2004/0058956 | A1 | 3/2004 | Akiyama et al. |
| 2004/0072889 | A1 | 4/2004 | Masferrer |
| 2004/0096436 | A1 | 5/2004 | Carson et al. |
| 2004/0152672 | A1 | 8/2004 | Carson et al. |
| 2004/0247600 | A1 | 12/2004 | Leoni |
| 2005/0020615 | A1 | 1/2005 | Rubino |
| 2005/0060028 | A1 | 3/2005 | Horres et al. |
| 2005/0176678 | A1 | 8/2005 | Horres et al. |
| 2006/0051412 | A1 | 3/2006 | Petereit et al. |
| 2006/0128777 | A1 | 6/2006 | Bendall et al. |
| 2006/0159713 | A1* | 7/2006 | Brittain et al. ................ 424/400 |
| 2007/0116729 | A1 | 5/2007 | Palepu |
| 2009/0264488 | A1 | 10/2009 | Cooper et al. |

FOREIGN PATENT DOCUMENTS

| CN | 101119708 A | 2/2008 |
| DE | 34727 | 12/1964 |
| DE | 80967 | 4/1971 |
| DE | 159289 | 3/1983 |
| DE | 159877 | 4/1983 |
| DE | 293808 | 9/1991 |
| DE | 10016077 | 12/2001 |
| DE | 10306724 | 9/2003 |
| DE | 10304403 | 8/2004 |
| EP | 0656211 | 6/1995 |
| EP | 1354952 | 10/2003 |
| EP | 1444989 | 8/2004 |
| JP | 04-506659 | 11/1992 |
| WO | WO 2009/013289 | 11/1990 |
| WO | WO 96/28148 | 9/1996 |
| WO | WO 03/066027 | 8/2003 |
| WO | WO 03/081238 | 10/2003 |

(Continued)

OTHER PUBLICATIONS

Aivado et al., "Bendamustine in the treatment of chronic lymphocytic leukemia: Results and future perspectives", Seminars in Oncology, Aug. 2002, 29(4), 19-22, Suppl. 13.
Author Unknown, "Ribomustin: Bendamustine Product Monograph", Ribosepharm GMBH, Munchen, Germany, Jan. 2002, 3-54.
Author Unknown, "Ribomustin: Bendamustine Product Monograph", Ribosepharm GMBH, Munchen, Germany, Mar. 2005, 3-73.
Barman et al., "Bendamustine" Drugs, 2001, 61(5), 631-638, Auckland, New Zealand.
Berge et al., "Pharmaceutical Salts", Journal of pharmaceutical sciences, Jan. 1977, 66(1), 1-19.
Bremer, "High Rates of Long-lasting remissions after 5-day bendamustine Chemotherapy Cycles in Pre-Treated low-grade non-hodgkin's-lymphomas", Journal of Cancer Research and Clinical Oncology, Nov. 2002, 128(11), 603-609.

(Continued)

*Primary Examiner* — Dennis Heyer
(74) *Attorney, Agent, or Firm* — Baker & Hostetler LLP

(57) ABSTRACT

Novel solid forms of bendamustine hydrochloride are described, as well as methods of their preparation and use.

22 Claims, 15 Drawing Sheets

(56) References Cited

FOREIGN PATENT DOCUMENTS

| | | |
|---|---|---|
| WO | WO 03/086470 | 10/2003 |
| WO | WO 03/094990 | 11/2003 |
| WO | WO 2006/076620 | 7/2006 |
| WO | WO 2009/120386 | 10/2009 |

OTHER PUBLICATIONS

Brittain, "Drugs and the Pharmaceutical Sciences," vol. 95, 1999, Polymorphism in Pharmaceutical Solids, pp. I-V, 228-239, XP003030775.

Byrn et al., "Pharmaceutical Solids: A Strategic Approach to Regulatory Consideration", Pharmaceutical Research, Jul. 1995, 12(7), 945-954.

Chow et al., "Anti-CD20 Antibody (DEC-C2B8, rituximab) enhances efficiency of cytotoxic drugs on neoplastic lymphocytes in vitro: Role of Cytokines complement and caspases", Hematologica, Jan. 2002, 87(1), 33-43.

Chow et al., "In AML Cell Lines Ara-C combined with Purine Analogues is able to Exert Synergistic as well as Antagnostic Effects on Proliferation Apoptosis and Disruption of Mitochondrial Membrane Potential", Leukemia & Lymphoma, 2003, 44(1), 165-173.

Chow et al., "In Vitro Induction of Apoptosis of Neoplastic Cells in Low-Grade non-Hodgkin's Lymphomas by Combination of established cytotoxic drugs with bendamustine", Hematologica, May 2001, 86(5), 485-493.

Chow et al., "Synergistic effects of chemotherapeutic drugs in lymphoma cells are associated with down-regulation of inhibitor of apoptosis proteins (IAPs), prostate-apoptosis-response-gene 4(Par-4), death-associated protein (Dazz) and with enforced caspase activation", Biochemical Pharmacology, Jan. 2003, 66(5), 711-724.

Diehl et al., "Bendamustine in the Treatment of Hematologic Malignancies", Semin. Oncol., Aug. 2002, 29(4), 1-3, Suppl. 13, Saundes, Philadelphia, PA.

EC Safety Data Sheet: Ribomustin® in http://www.docstoc.com/docs/22323231/EC-Safety-Data-Sheet-Bendamustin (published: Jul. 3, 1998; updated Mar. 1, 2007).

EC Safety Data Sheet: Ribomustin® in www.asl.ri.it/staff/prevenzione/documentazione/Chemio/Ribomustin%20scheda%20di%2Osicurrezza.pdf (Retrieved from the internet Jun. 11, 2013).

Fichtner et al., "Antineoplastic activity and toxicity of some alkylating cytostatics (cyclophosphamide, CCNU, cytostasan) encapsulated in liposomes in different murine tumor models", Journal of Microencapsulation, Jan. 1986, 3(2), 77-87.

Friedberg et al., "Bendamustine in patients with Rituximab-refractory indolent and transformed non-hodgkin's lymphoma", Journal of Clinical Oncology, Jan. 10, 2008, vol. 26, No. 2, pp. 204-210.

Friedberg et al., Bendamustine HCI (TRENDA™) Treatment Results in High Rates of Objective Response in Patients with Rituximab-Refractory and Alkylator-Refractory Indolent B-Cell Non-Hodgkin's Lymphoma (NHL): Results from a Phase II Multicenter Single—Agent Study (SDX-105-01), in Blood 106 (11), 2005 (Abstract 229).

Gandhi, Varsha, "Metabolism and mechanisms of action of bendamustine: Rationales for combination therapies", Seminars in Oncology, Aug. 2002, 29(4), 4-11, Suppl. 13.

Goodman et al., The Pharmacological Basis of Therapeutics, 1985, 7$^{th}$ edition, Macmillan publishing company, New York.

Gust et al., "Investigation on the Stability of Bendamustin, a Cytostatic Agent of the Nitrogen Mustard Type I. Synthesis, Isolation and Characterization of Reference Substances", Monatshefte fur Chemie, 1997, 128(3), 291-299.

Heider et al., "Efficacy and Toxicity of bendamustine in patients with relapsed low-grade non-Hodgkin's lymphomas", Anti-Cancer Drugs, 2001, 12(9), 725-729.

Kath et al., "Bendamustine Monotherapy in advanced and refractory chronic lymphocytic Leukemia", Journal of Cancer Research and Clinical Oncology, 2001, 127(1), 48-54.

Koenigsman et al., "Fludarabine and Bendamustine in Refractory and Relapsed Indolent Lymphoma—a Multicenter Phase I/II Trial of the East German Society of Hematology and Oncology (OSHO)", Leukemia & Lymphoma, 2004, 45(9), 1821-1827.

Kollmannsberger et al., "Phase II study of Bendamustine in Patients with relapsed or cisplatin-refractory germ cell Cancer", Anti-Cancer Drugs, 2000, 11(7), 535-539.

Konstantinov et al., "Cytotoxic Efficacy of Bendamustine in Human Leukemia and Breast Cancer cell lines", Journal of Cancer Research and Clinical Oncology, 2002, 128(5), 271-278.

Köster et al., "Carboplatin in combination with bendamustine in previously untreated patients with extensive-stage small lung cancer (SCLC)", Clinical Drug Investigation, 2004, 24(10), 611-618.

Leoni et al., "Sdx-105 (Trenda), Active in Non-Hodgkin's Lymphoma Cells, Induces the Mitotic Catastrophe Death Pathway", Blood, 2004, 104(11), (Abstract).

Maas, "Stability of Bendamustine Hydrochloride in Infusion Solutions", 1994, 49(10), 9 pages.

Morissette et al., "High-throughput crystallization: polymorphs, salts, co-crystals and solvates of pharmaceutical solids", Advanced Drug Delivery Reviews, Feb. 2004, 56(3), 275-300.

Niemeyer et al., "SDX-105 (bendamustine) is a clinically active chemotherapeutic agent with a distinct mechanism of action", Proc Annu Meet Am Assoc Cancer Res, Mar. 2004, 45, 1st ed., 2 pages.

Nowak et al., "Upon Drug-Induced Apoptosis in Lymphoma Cells X-linked Inhibitor of Apoptosis (XIAP) Translocates from the Cytosol to the Nucleus", Leukemia & Lymphoma, Jul. 2004, 45(7), 1429-1436.

Ozegowski et al., "IMET 3393, gamma-(1-methyl-5-bis-(β-chloräthyl)-amino-benzimidazolyl(2)-buttersäure-hydrochlorid, ein neues Zytostatikum aus der Reihe der Benzimidazol-Loste", Zbl Pharm., 1971;110, Heft 10, 1013-1019.

Ponisch et al., "Bendamustine in the treatment of Multiple Myeloma: Results and future perspectives", Seminars in Oncology, Aug. 2002, 29(4), 23-26, Suppl. 13.

Preiss et al., "Pharmacokinetics of bendamustin (Cytostasan) in patients", Pharmazie, Mar. 1985, 40(11), 782-784.

Remington: Pharmaceutical Sciences, 1990, Mack Publishing company, Easton, Pennsylvania.

Ribosepharm, "Product monograph ribosepharm passage", Product Monograph, Ribosepharm, Jan. 1, 2005, pp. 3-73.

Rummel et al., "Bendamustine in the Treatment of Non-Hodgkin's Lymphoma: Results and Future Perspectives", Seminars in Oncology, Suppl. 13, Aug. 2002, 29(4), 27-32.

Rummel et al., "In Vitro Studies with Bendamustine: Enhanced Activity in Combination with Rituximab", Seminars in Oncology, Suppl. 13, Aug. 2002, 29(4), 12-14.

Scasnar et al., "Radiochemical Assay of Stability of 14C-Cytostasan Solutions During Preparation and Storage", Journal of Radioanalytical and Nuclear Chemistry, 1998, 121(2), 489-497.

Scasnar et al., "Stability Studies of 14C-Cytostasan® solutions and its extraction using dicarbolide of cobalt", Phamazie, Mar. 1988, 43, 176-179.

Schmidt-Hieber et al., "A Phase II Study of bendamustine Chemotherapy as Second-line treatment in metastatic uveal Melanoma", Melanoma Research, 2004, 14(6), 439-442.

Schoffski, "Repeated Administration of Short Infusions of Bendamustine: A phase I study in Patients with Advanced Progressive Solid Tumors", Journal of Cancer Research and Clinical Oncology, 2000, 126(1), 41-47.

Schrijvers et al., "Phase I study with bendamustine: An update", Seminars in Oncology, Suppl. 13, 2002, 29(4), 15-18.

Schwanen et al., "In Vitro Evaluation of Bendamustine Induced Apoptosis in B-Chronic Lymphocytic Leukemia", Leukemia, Oct. 2002, 16(10), 2096-2105.

Strumberg et al., "Bendamustine Hydrochloride Activity against doxorubicin-resistant Human Breast Carcinoma Cell Lines", Anti-Cancer Drugs, 1996, 7(4), 415-421.

Weide et al., "Bendamustine Mitoxantrone and Rituximab (BMR): A New effective regimen for refractory or relapsed indolent lymphomas", Leukemia & Lymphoma, 2002, 43(2), 327-331.

(56) References Cited

OTHER PUBLICATIONS

Weide et al., "Bendamustine/Mitoxantrone/Rituximab (BMR) : A very Effective, well tolerated Outpatient Chemoimmunotherapy for relapsed and refractory CD20-positive Indolent Malignancies Final Results of a Pilot Study", Leukemia & Lymphoma, 2004, 45(12), 2445-2449.

Weidmann et al., "Bendamustine is Effective in Relapsed or Refractory Aggressive non-Hodgkin's Lymphoma", Annals of Oncology, 2002, 13(8), 1285-1289.

Werner et al., "Hydrolyseprodukte des Cancerostaticums Cytostasan (Bendamustin)", Pharmazie, 1987, 42, 272-273.

Zulkowski et al., "Regression of Brain Metastases from Breast Carcinoma after Chemotherapy with bendamustine", Journal of Cancer Research and Clinical Oncology, 2002, 128(2), 111-113.

* cited by examiner

SOLID FORMS OF BENDAMUSTINE HYDROCHLORIDE

CROSS-REFERENCE TO RELATED APPLICATION

This application is a continuation of pending U.S. application Ser. No. 13/874,575, filed May 1, 2013, which is a continuation of U.S. application Ser. No. 13/301,979, now U.S. Pat. No. 8,445,524, filed Nov. 22, 2011, which is a continuation of U.S. application Ser. No. 12/411,929, filed Mar. 26, 2009, now abandoned, which claims the benefit of U.S. Provisional Application No. 61/039,752, filed Mar. 26, 2008. The disclosures of these prior applications are incorporated herein by reference in their entireties for all purposes.

FIELD OF THE INVENTION

This invention pertains to bendamustine-containing compositions, pharmaceutical compositions comprising bendamustine, processes to reproducibly make them, and methods of treating patients using them.

BACKGROUND OF THE INVENTION

Active pharmaceutical ingredients (APIs) can be prepared in a variety of different forms, for example, chemical derivatives, solvates, hydrates, co-crystals, or salts. APIs may also be prepared in different solid forms, in that they may be amorphous, may exist as different crystalline polymorphs, and/or in different solvation or hydration states. By varying the form of an API, it is possible to vary the physical properties thereof. For instance, solid forms of an API typically have different solubilities such that a more thermodynamically stable solid form is less soluble than a less thermodynamically stable solid form. Solid forms can also differ in properties such as shelf-life, bioavailability, morphology, vapor pressure, density, color, and compressibility. Accordingly, variation of the solid state of an API is one of many ways in which to modulate the physical and pharmacological properties thereof.

Bendamustine, 4-{5-[Bis(2-chloroethyl)amino]-1-methyl-2-benzimidazolyl}butyric acid:

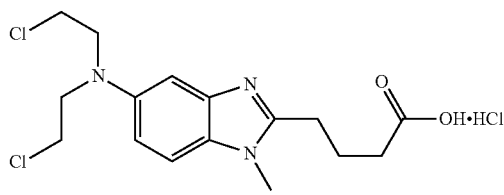

Bendamustine Hydrochloride was initially synthesized in 1963 in the German Democratic Republic (GDR) and was available from 1971 to 1992 there under the tradename Cytostasan®. See, e.g., W. Ozegowski and D. Krebs, IMET 3393 γ-[1-methyl-5-bis-(β-chloroethyl)-aminobenzimidazolo-(2)]-butyryl chloride, a new cytostatic agent of the group of benzimidazole nitrogen mustards. Zbl. Pharm. 110, (1971) Heft 10, 1013-1019, describing the synthesis of bendamustine hydrochloride monohydrate. Since that time, it has been marketed in Germany under the tradename Ribomustin®. Bendamustine is an alkylating agent that has been shown to have therapeutic utility in treating diseases such as chronic lymphocytic leukemia, Hodgkin's disease, non-Hodgkin's lymphoma, multiple myeloma, and breast cancer.

While bendamustine has been demonstrated as efficacious, it is known to be unstable, especially in aqueous solutions, leading to technical difficulties in its preparation and administration. Researchers, therefore, have investigated methods of improving the preparation and stability of bendamustine and its formulations. For example, German (GDR) Patent No. 159877 discloses a method for preparing bendamustine free base by reaction of the bis-hydroxyl precursor with thionyl chloride followed by recrystallization from water.

German (GDR) Patent No. 34727 discloses a method of preparing derivatives of bendamustine. The described derivatives differ from bendamustine in the substitution at the 1-position.

German (GDR) Patent No. 80967 discloses an injectable preparation of bendamustine hydrochloride monohydrate, ascorbic acid, and water. GDR 80967 describes that lyophilization of compounds such as bendamustine is only possible if the compound is of sufficient stability that it can withstand the processing conditions. The preparation described in GDR 80967 is not lyophilized.

German (GDR) Patent No. 159289 discloses a ready-to use, injectable solution of bendamustine hydrochloride that avoids lyophilization. GDR 159289 describes an anhydrous solution of bendamustine hydrochloride in 1,2-propylene glycol or ethanol.

U.S. application Ser. No. 11/330,868, filed Jan. 12, 2006, assigned to Cephalon, Inc., Frazer, Pa., discloses methods of preparing lyophilized pharmaceutical compositions comprising bendamustine hydrochloride.

In light of the potential benefits of different solid forms of APIs and in light of the efficacy of bendamustine, a need exists to identify and prepare novel solid forms of bendamustine hydrochloride.

SUMMARY OF THE INVENTION

Solid forms of bendamustine hydrochloride are described, as well as methods of their preparation. For example, in some embodiments, the invention is directed to a solid form of bendamustine hydrochloride that comprises at least one of bendamustine hydrochloride Form 1, bendamustine hydrochloride Form 3, bendamustine hydrochloride Form 4, amorphous bendamustine hydrochloride, or a mixture thereof. This solid form of bendamustine hydrochloride may be one that produces an X-ray powder diffraction pattern comprising one or more of the following reflections: 25.1, 24.9, 22.9, 22.0, and/or 14.1±0.2 degrees 2θ, or that produces an X-ray powder diffraction pattern further comprising one or more of the following reflections: 16.8, 17.5, 18.5, 24.9, and/or 28.3±0.2 degrees 2θ. Alternatively, the solid form of bendamustine hydrochloride may produce an X-ray powder diffraction pattern comprising one or more of the following reflections: 26.1, 27.9, and/or 28.1±0.2 degrees 2θ, or that further produces an X-ray powder diffraction pattern further comprising one or more of the following reflections: 10.6, 15.6, and/or 19.8±0.2 degrees 2θ. Other embodiments may produce an X-ray powder diffraction pattern comprising one or more of the following reflections: 10.8, 15.5, 20.5, and/or 23.6±0.2 degrees 2θ, or that produce an X-ray powder diffraction pattern further comprising one or more of the following reflections: 10.3, 19.6, 20.7, 21.2, 25.8 and/or 27.6±0.2 degrees 2θ.

Another embodiment of the invention is directed to compositions comprising a solid form of bendamustine hydrochloride, such as described above. In certain embodiments, the composition is a pharmaceutical composition that further comprises at least one pharmaceutically acceptable excipient. In other embodiments, the composition is a lyophilized composition. In certain embodiments the composition comprises a single solid form of bendamustine hydrochloride and is substantially free of other solid forms. Alternatively, the composition may contain a mixture of solid forms, such as a mixture of a crystalline form of bendamustine hydrochloride and amorphous bendamustine. Thus, the composition may, for example, be a lyophilized composition that produces an X-ray powder diffraction pattern comprising one or more of the following reflections: 7.98, 10.58, 15.43, 19.64, and/or 19.89±0.2 degrees 2θ.

Methods of preparing the compositions, and methods of using same for use in treating chronic lymphocytic leukemia, Hodgkin's disease, non-Hodgkin's lymphoma, multiple myeloma or breast cancer are also described.

DETAILED DESCRIPTION OF ILLUSTRATIVE EMBODIMENTS

Figure 1:
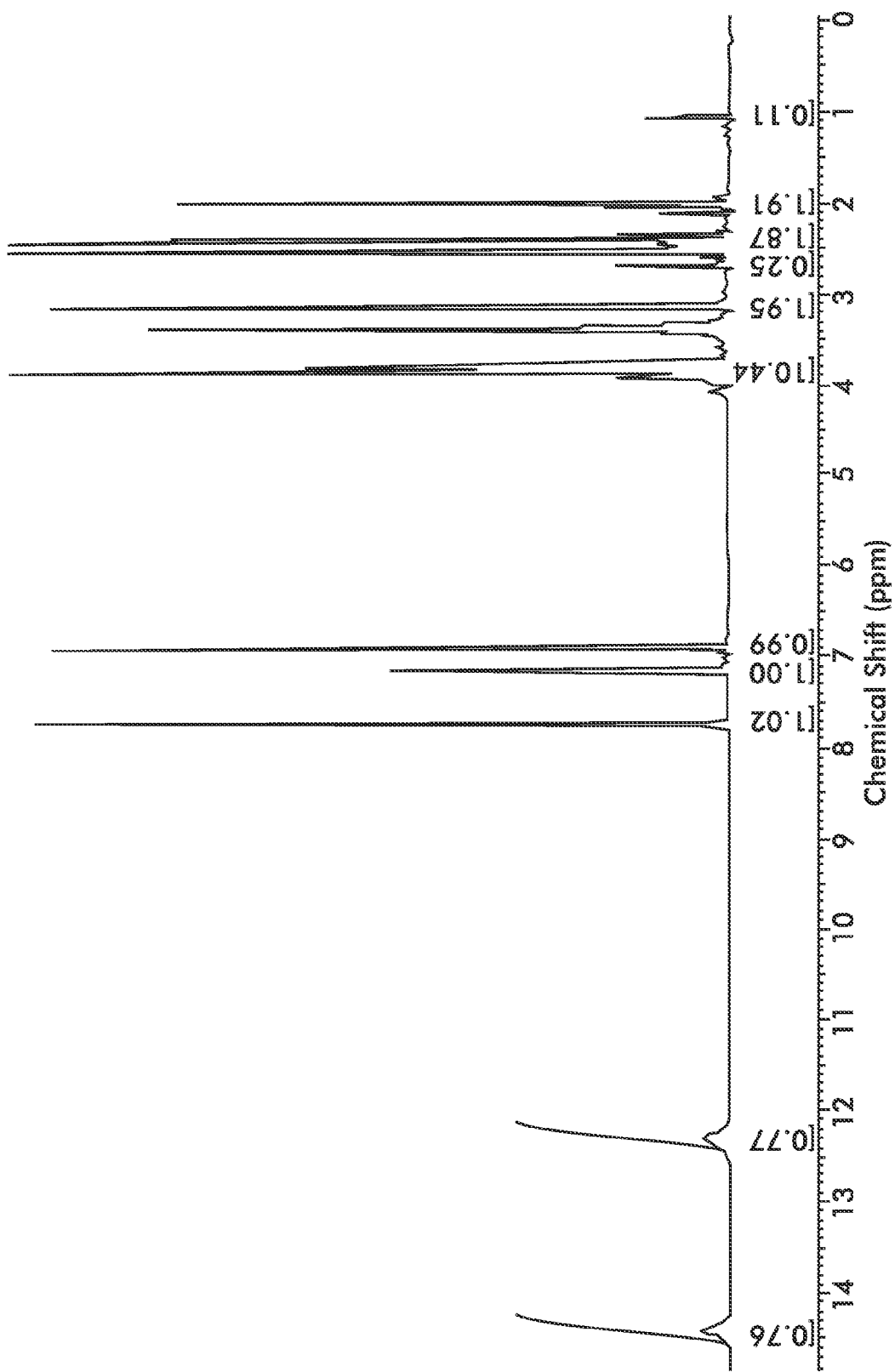
FIG. 1 is a $^1$H NMR spectrum of bendamustine hydrochloride

Four polymorphs of crystalline bendamustine hydrochloride are disclosed herein (referred to herein as Form 1, Form 2, Form 3, and Form 4). Also described is amorphous (i.e., non-crystalline) bendamustine hydrochloride. Spectral data relating to these solid forms of bendamustine hydrochloride is depicted in FIGS. 1-14, and methods of preparing each of these forms is presented In preferred embodiments are solid forms of bendamustine hydrochloride that comprise Form 1, Form 2, Form 3, Form 4, or mixtures thereof. More preferred embodiments are solid forms of bendamustine hydrochloride that are Form 1, Form 3, Form 4, amorphous bendamustine hydrochloride, or mixtures thereof. In other embodiments, solid forms of the invention may further comprise bendamustine hydrochloride Form 2. These polymorphic solid forms may be identified, for example, by X-ray powder diffraction and characterized by one, two, three, four, five, or more reflection peaks that are characteristic of each polymorphic form. The four crystalline polymorphs (Form 1, Form 2, Form 3, Form 4) and amorphous bendamustine hydrochloride can also be identified by reference to their DSC thermograms, TGA thermograms, and/or GVS traces, which are set forth in FIGS. 1-14. Methods of making solid forms of bendamustine, including each of the described polymorphs, or a mixture of polymorphs, and amorphous bendamustine hydrochloride can be preformed using the techniques described herein.

Any of the solid forms of bendamustine hydrochloride described herein can be a component of a composition comprising bendmustine hydrochloride. In some embodiments, these compositions comprising at least one of the solid forms of bendamustine hydrochloride described herein are substantially free of other solid forms of bendamustine hydrochloride.

Certain of the preferred embodiments of the invention may be characterized, at least in part, by X-ray Powder Diffraction. As is known in the art, crystalline solids produce a distinctive diffraction pattern of peaks, represented in what is referred to as a diffractogram. The peak assignments for a given crystalline material, for example, degree 2θ values, may vary slightly, depending on the instrumentation used to obtain the diffractogram and certain other factors, for example, sample preparation. Nevertheless, these variations should not be more than +/−0.2 degrees 2θ and the relative spacing between the peaks in the diffractogram will always be the same, regardless of the instrumentation used or the method of sample preparation, and the like.

In preferred embodiments, compositions of the invention are pharmaceutical compositions that further comprise at least one pharmaceutically acceptable excipient. Preferred excipients include, for example, sodium phosphate, potassium phosphate, citric acid, tartaric acid, gelatin, glycine, mannitol, lactose, sucrose, maltose, glycerin, dextrose, dextran, trehalose, hetastarch, or a mixture thereof. A more preferred pharmaceutical excipient is mannitol.

In another embodiment of the invention are pharmaceutical compositions comprising Form 1, Form 2, Form 3, Form 4, or mixtures thereof, of bendamustine hydrochloride. In more preferred embodiments are compositions, preferably pharmaceutical compositions, that comprise Form 1, Form 3, Form 4, amorphous, or mixtures thereof, of bendamustine hydrochloride. In other embodiments, the pharmaceutical compositions further comprise Form 2 or bendamustine hydrochloride. More preferred embodiments of the invention are pharmaceutical compositions comprising one or more of Form 1, Form 2, Form 3, and Form 4 with amorphous bendamustine hydrochloride.

In another embodiment of the invention are lyophilized compositions comprising at least one solid form of bendamustine hydrochloride as described herein. Preferred lyophilized compositions of the invention include those that comprise a mixture of amorphous bendamustine hydrochloride and at least one crystalline form of bendamustine hydrochloride. More preferred lyophilized compositions of the invention include those that comprise a mixture of amorphous bendamustine hydrochloride and bendamustine hydrochloride Form 4.

Lyophilized compositions of the invention can further include at least one pharmaceutically acceptable excipient. Preferred excipients include, for example, sodium phosphate, potassium phosphate, citric acid, tartaric acid, gelatin, glycine, mannitol, lactose, sucrose, maltose, glycerin, dextrose, dextran, trehalose, hetastarch, or a mixture thereof. A more preferred pharmaceutical excipient is mannitol. A preferred lyophilized composition of the invention comprises a mixture of amorphous bendamustine hydrochloride, bendamustine hydrochloride Form 4, and at least one pharmaceutically acceptable excipient that is preferably mannitol. More preferred are lyophilized compositions consisting essentially of amorphous bendamustine hydrochloride, bendamustine hydrochloride Form 3, and mannitol. (See, e.g., FIG. 14)

Form 1 was characterized as a white powder consisting of lath shaped particles. Form 1 was crystalline by X-ray Powder Diffraction (XRPD), the $^1$H NMR spectrum was consistent with the structure of the molecule, and the purity was 97.2%. Thermal analysis showed an endotherm with onset 167° C. (ΔH 103 J/g) corresponding to a melting event. (Peak=170° C.). Degradation occurred above this temperature. The sample became amorphous by XRPD (FIG. 13) on heating to 180° C. (melt) and remained amorphous on cooling to ambient temperature. Form 1 was found to have low hygroscopicity, showing a 0.7% weight increase between 0 and 90% relative humidity (RH). This did not lead to a significant change in XRPD pattern upon reanalysis under ambient conditions. There were no significant changes during 1 week of storage at 40° C./75% RH or 3 weeks of storage at 40° C./11% RH. The data from the XRPD is shown below.

XRPD Data for Bendamustine HCl Form 1

| Angle (2-Theta) | d value (Angstrom) | Intensity (Counts) | Intensity (%) |
|---|---|---|---|
| 8.349 | 10.59033 | 110 | 6.8 |
| 13.503 | 6.55757 | 129 | 8 |
| 14.049 | 6.30377 | 394 | 24.5 |
| 16.824 | 5.26978 | 190 | 11.8 |
| 17.51 | 5.06473 | 172 | 10.7 |
| 18.452 | 4.80825 | 167 | 10.4 |
| 20.239 | 4.38767 | 130 | 8.1 |
| 20.904 | 4.24957 | 257 | 16 |
| 21.544 | 4.12484 | 295 | 18.3 |
| 21.972 | 4.04537 | 980 | 60.9 |
| 22.354 | 3.97705 | 210 | 13.1 |
| 22.922 | 3.87977 | 1213 | 75.4 |
| 23.305 | 3.81696 | 215 | 13.4 |
| 23.672 | 3.7586 | 317 | 19.7 |
| 24.851 | 3.58278 | 833 | 51.8 |
| 25.122 | 3.54475 | 1608 | 100 |
| 25.858 | 3.44558 | 173 | 10.7 |
| 26.35 | 3.38229 | 254 | 15.8 |
| 27.082 | 3.29256 | 437 | 27.2 |
| 27.591 | 3.23295 | 343 | 21.3 |
| 28.327 | 3.15055 | 704 | 43.8 |
| 29.155 | 3.06303 | 144 | 8.9 |
| 29.356 | 3.04246 | 151 | 9.4 |

Form 1 converted to a hydrate of bendamustine hydrochloride (Form 2) during 2 months of storage at 25° C./94% RH. The aqueous solubility was 4.5 mg/ml with a solution pH of 2.16, but significant degradation occurred to the sample in this experiment. The pKa values found for this material by UV in aqueous conditions were 0.88 (Base), 4.17 (Acid) and 6.94 (Base). The LogP value found was 1.10 with a LogD at pH7.4 of 0.68. The single crystal structure of this form was obtained:

A View of the Single Crystal Structure of Form 1 of Bendamustine HCl

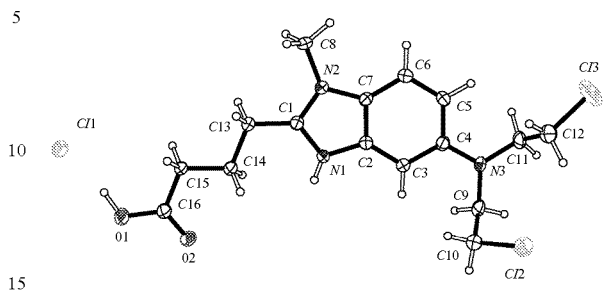

Unit Cell Data and Final Residuals for Bendamustine Hydrochloride Form 1

| Crystal Data | Form 1 | |
|---|---|---|
| Chemical Formula | [C$_{16}$H$_{22}$Cl$_2$N$_3$O$_2$] | |
| Molecular weight | 394.7 | |
| Crystal system | monoclinic | |
| Space group | C2/c | |
| | −193° C. | 22° C. |
| a (Å) | 23.0847(4) | 23.080(5) |
| b (Å) | 6.80560(10) | 6.882(2) |
| c (Å) | 25.5054(5) | 25.504(6) |
| beta (°) | 114.2480(10) | 114.09(1) |
| volume (Å$^3$) | 3653.52(11) | 3693.8(4) |
| Z | 8 | |
| Density (calculated) (g/ml) | 1.435 | 1.419 |
| R(Fobs) | 0.0382 | |
| wR(all, Fsq) | 0.1392 | |
| S | 1.006 | |

Form 1 was shown to be more stable to degradation in light, as compared to Form 2.

Form 2, a monohydrate, was characterized as a white powder consisting of rod shaped particles. Form 2 was crystalline by XRPD and the purity was 98.3%. The XRPD data is depicted below.

XRPD Data for Bendamustine HCl Form 2

| Angle (2-Theta) | d value (Angstrom) | Intensity (Counts) | Intensity (%) |
|---|---|---|---|
| 10.169 | 8.69836 | 167 | 8.5 |
| 10.638 | 8.31653 | 1274 | 64.6 |
| 11.443 | 7.73271 | 155 | 7.9 |
| 12.46 | 7.10378 | 162 | 8.2 |
| 13.662 | 6.48137 | 186 | 9.4 |
| 15.055 | 5.88491 | 234 | 11.9 |
| 18.828 | 4.71319 | 631 | 32 |
| 19.724 | 4.50101 | 206 | 10.5 |
| 20.115 | 4.41437 | 955 | 48.4 |
| 20.451 | 4.34275 | 1017 | 51.6 |
| 20.95 | 4.24033 | 654 | 33.2 |
| 21.45 | 4.14261 | 371 | 18.8 |
| 22.15 | 4.01325 | 301 | 15.3 |
| 23.105 | 3.84943 | 1972 | 100 |
| 23.449 | 3.79375 | 373 | 18.9 |
| 23.859 | 3.72952 | 236 | 12 |
| 24.101 | 3.6926 | 271 | 13.7 |
| 24.511 | 3.6317 | 317 | 16.1 |
| 24.849 | 3.58309 | 290 | 14.7 |
| 25.204 | 3.53342 | 434 | 22 |
| 25.498 | 3.49344 | 320 | 16.2 |
| 25.843 | 3.44749 | 257 | 13 |

XRPD Data for Bendamustine HCl Form 2

| Angle (2-Theta) | d value (Angstrom) | Intensity (Counts) | Intensity (%) |
|---|---|---|---|
| 26.538 | 3.35877 | 788 | 40 |
| 27.248 | 3.27289 | 382 | 19.4 |
| 27.695 | 3.22103 | 402 | 20.4 |
| 28.018 | 3.18459 | 243 | 12.3 |
| 28.256 | 3.15834 | 248 | 12.6 |
| 28.487 | 3.13331 | 297 | 15 |
| 29.046 | 3.07423 | 352 | 17.9 |
| 29.255 | 3.0527 | 244 | 12.4 |

Thermal analysis showed a broad endotherm with onset at 37° C. due to water loss. This corresponded with a 5.2% weight loss on heating between ambient and 100° C., equating to loss of 1.2 equivalents of water, and a conversion to Form 4. The sample showed a 4% uptake between 10 and 15% RH during GVS analysis, equating to 1 mole of water. On XRPD re-analysis after the GVS cycles a peak at 14° 2θ was observed. This peak is indicative of the presence of Form 1, suggesting that partial conversion occurred during the GVS experiment. A similar XRPD trace was obtained after storing pure Form 1 at 25° C./94% RH for one month as the sample was in the process of converting to Form 2. There were no significant changes to the sample by XRPD after one month of storage at 40° C./75% RH, but the sample became less crystalline during one month at 40° C./11% RH. A significant decrease in crystallinity and purity was observed during light stability experiments.

A review of the prior art indicates that a monohydrate of bendamustine hydrochloride has been prepared previously. See, W. Ozegowski and D. Krebs, supra. That monohydrate has a reported melting point of 152-56° C. This melting point is similar to that observed with bendamustine hydrochloride Form 2, which has an observed melting point of 153-157° C. While not conclusive, it is possible that Form 2 and the bendamustine hydrochloride monohydrate reported in the prior art are the same polymorph. But as no further characterization details, for example XRPD, have been reported or are available for the bendamustine hydrochloride monohydrate reported in the prior art, it is not known whether the monohydrate reported previously was Form 2 bendamustine hydrochloride.

Storage of Form 1, Form 2 and 1:1 mixtures for up to 6 weeks only showed a conversion of Form 1 to 2 after storage at high humidity (60° C./95% RH, 25° C. 94% RH and possibly 4° C./88% RH for 6, 6 and 2 weeks respectively). No conversion of Form 2 to Form 1 was noted in these studies after 6 weeks. Kinetic factors make it very difficult to determine the absolute thermodynamic stability in the 6 weeks studied and both forms were kinetically stable for 6 weeks at 4° C./34 to 76% RH, 25° C./43 to 75% RH and 60° C./11 to 75% RH.

Form 3 was characterized as a white powder which was partially crystalline by XRPD. No significant changes were observed on XRPD re-analysis after 1 month of storage under ambient conditions, but conversion to Form 2 occurred during 1 week at 40° C./75% RH. The purity was 95.9%. XRPD data for Form 3 is shown below.

XRPD Data for Bendamustine HCl Form 3

| Angle (2-Theta) | d value (Angstrom) | Intensity (Counts) | Intensity (%) |
|---|---|---|---|
| 3.85 | 22.95248 | 13.6 | 2.1 |
| 5.384 | 16.41406 | 16.3 | 2.5 |
| 5.75 | 15.37009 | 12.1 | 1.9 |
| 7.892 | 11.20261 | 40.4 | 6.2 |
| 10.575 | 8.36538 | 177 | 27.2 |
| 13.426 | 6.59478 | 30.1 | 4.6 |
| 13.636 | 6.49389 | 10.9 | 1.7 |
| 13.993 | 6.32893 | 36.3 | 5.6 |
| 14.7 | 6.0261 | 7.62 | 1.2 |
| 15.547 | 5.69958 | 121 | 18.6 |
| 15.734 | 5.63243 | 41.4 | 6.4 |
| 17.35 | 5.1112 | 25 | 3.8 |
| 17.608 | 5.0369 | 14.1 | 2.2 |
| 18.594 | 4.77186 | 55.1 | 8.5 |
| 18.85 | 4.70772 | 85.8 | 13.2 |
| 19.428 | 4.56899 | 80.2 | 12.3 |
| 19.749 | 4.49541 | 436 | 67 |
| 19.995 | 4.44068 | 173 | 26.6 |
| 21.3 | 4.17144 | 216 | 33.3 |
| 22.11 | 4.02037 | 233 | 35.8 |
| 23.328 | 3.81319 | 409 | 63 |
| 25.449 | 3.49996 | 393 | 60.5 |
| 25.571 | 3.48361 | 355 | 54.6 |
| 25.733 | 3.46204 | 294 | 45.3 |
| 26.083 | 3.41636 | 650 | 100 |
| 26.394 | 3.37675 | 305 | 46.9 |
| 26.61 | 3.34983 | 279 | 43 |
| 27.852 | 3.2032 | 393 | 60.5 |
| 27.977 | 3.1892 | 403 | 62 |
| 28.109 | 3.17455 | 392 | 60.3 |
| 29.039 | 3.07492 | 195 | 30 |

Form 4 was characterized as a white powder which was crystalline by XRPD. Thermal analysis showed an endotherm due to melting at 153° C. (Peak=157° C.). Form 4 converted to Form 2 during 24 hours under ambient conditions. XRPD data for Form 4 is depicted below.

XRPD Data for Bendamustine HCl Form 4

| Angle (2-Theta) | d value (Angstrom) | Intensity (Counts) | Intensity (%) |
|---|---|---|---|
| 3.86 | 22.88824 | 63.2 | 4.6 |
| 7.794 | 11.34336 | 120 | 8.8 |
| 10.267 | 8.61623 | 293 | 21.4 |
| 10.831 | 8.16867 | 1297 | 95 |
| 11.624 | 7.61314 | 149 | 10.9 |
| 11.804 | 7.4972 | 134 | 9.8 |
| 12.806 | 6.91286 | 169 | 12.4 |
| 14.077 | 6.29121 | 209 | 15.3 |
| 15.521 | 5.70899 | 376 | 27.5 |
| 16.038 | 5.5262 | 135 | 9.9 |
| 18.748 | 4.73313 | 168 | 12.3 |
| 19.636 | 4.52097 | 455 | 33.3 |
| 20.447 | 4.34345 | 1021 | 74.7 |
| 20.734 | 4.28411 | 793 | 58.1 |
| 21.227 | 4.18563 | 557 | 40.8 |
| 21.865 | 4.06498 | 202 | 14.8 |
| 22.263 | 3.99311 | 198 | 14.5 |
| 23.1 | 3.85031 | 306 | 22.4 |
| 23.579 | 3.77323 | 1366 | 100 |
| 23.95 | 3.71555 | 513 | 37.5 |
| 24.39 | 3.64947 | 250 | 18.3 |
| 24.548 | 3.62633 | 237 | 17.3 |
| 25.477 | 3.49624 | 266 | 19.5 |
| 25.81 | 3.45184 | 659 | 48.3 |
| 26.559 | 3.35619 | 258 | 18.9 |
| 27.101 | 3.29025 | 363 | 26.6 |
| 27.627 | 3.22885 | 818 | 59.9 |
| 28.415 | 3.14102 | 364 | 26.6 |

Amorphous bendamustine hydrochloride had a glass transition temperature of about 50° C. and became gummy during 24 hours under ambient conditions, showing it is hygroscopic. Also, partial crystallization occurred during 1 week at 40° C./75% RH, possibly to a mixture of Forms 2 and 3. After subjection to GVS humidity cycle, amorphous bendamustine hydrochloride converted to Form 2.

Preferred pharmaceutical compositions of the invention comprise amorphous bendamustine hydrochloride. The bendamustine hydrochloride may be provided as compositions consisting primarily of an amorphous form of bendamustine hydrochloride or as compositions comprising amorphous bendamustine hydrochloride as well as a crystalline form, such as crystalline bendamustine hydrochloride Form 1, Form 2, Form 3, Form 4, or mixtures thereof. Preferred pharmaceutical compositions of the invention comprise bendamustine hydrochloride substantially free from crystalline bendamustine hydrochloride.

In preferred embodiments, pharmaceutical compositions comprising at least one of Form 1, Form 2, Form 3, Form 4, and amorphous bendamustine hydrochloride, as well as at least one pharmaceutically acceptable excipient, are provided. Preferably, the pharmaceutical compositions comprise at least one of Form 1, Form 3, Form 4, and amorphous bendamustine hydrochloride, as well as at least one pharmaceutically acceptable excipient. More preferred are pharmaceutical compositions that comprise amorphous bendamustine hydrochloride, Form 4, and at least one pharmaceutically acceptable excipient.

Pharmaceutically acceptable excipients are known in the art and include those described in, for example, U.S. application Ser. No. 11/267,010, the content of which is incorporate herein in its entirety. These pharmaceutical compositions may be prepared as injectables, either as liquid solutions or suspensions, as well as solid forms, for example, capsules, tablets, lozenges, pastilles, powders, suspensions, and the like.

In preferred embodiments, the pharmaceutical compositions are sublimed, preferably freeze-dried or lyophilized, compositions. Methods of preparing such sublimed, preferably freeze-dried or lyophilized, preparations of bendamustine hydrochloride that contain Form 1, Form 2, Form 3, Form 4, or a mixture thereof, are also within the scope of the invention. Methods of preparing such sublimed, preferably freeze-dried or lyophilized, preparations of bendamustine hydrochloride that contain Form 1, Form 3, Form 4, amorphous bendamustine hydrochloride, or a mixture thereof, are also within the scope of the invention. Methods of preparing such sublimed, preferably freeze-dried or lyophilized, preparations of bendamustine hydrochloride that further contain Form 2, are also within the scope of the invention.

Lyophilization involves the addition of water to a compound, followed by freezing of the resultant suspension or solution, and sublimation of the water from the compound. In preferred embodiments, at least one organic solvent is added to the suspension/solution. In other preferred embodiments, the suspension/solution further comprises a lyophilization excipient. The lyophilized preparations of bendamustine hydrochloride of the present invention may further comprise amorphous bendamustine hydrochloride.

In a typical lyophilization procedure, water, a pharmaceutically acceptable lyophilizing excipient, an organic solvent, and a compound are combined to form a solution, which is then sterilized, preferably using sterile filtration methodology. This solution is then lyophilized using standard lyophilization equipment and techniques.

While preferred embodiments of the present invention include lyophilization of bendamustine hydrochloride, it is envisioned that other sublimation techniques may also be used. For example, one or more of the described forms of bendamustine hydrochloride may be dissolved, dispersed or suspended in a solvent, the resulting mixture (be it a solution, dispersion or suspension) frozen, and the solvent removed by sublimation.

A lyophilization excipient can be any pharmaceutically acceptable excipient that, when used during the lyophilization process, results in a lyophilized product that has improved properties, for example, improved handling properties, solubility properties, and the like. A lyophilization excipient can be, for example, a bulking agent; suitable bulking agents are known in the art. Examples of suitable lyophilization excipients include, for example, sodium phosphate, potassium phosphate, citric acid, tartaric acid, gelatin, glycine, mannitol, lactose, sucrose, maltose, glycerin, dextrose, dextran, trehalose, hetastarch, or mixtures thereof. A lyophilization excipient may also comprise a pharmaceutically acceptable antioxidant, such as, for example, ascorbic acid, acetylcysteine, cysteine, sodium hydrogen sulfite, butyl-hydroxylanisole, butyl-hydroxytoluene, or alpha-tocopherol acetate. A preferred lyophilization excipient is mannitol.

Solvents for use in the present invention include water and organic solvents that form stable solutions with bendamustine hydrochloride without appreciably degrading the bendamustine, and which are capable of being evaporated/sublimed through lyophilization. Examples of suitable organic solvents include, for example, methanol, ethanol, n-propanol, iso-propanol, n-butanol, tert-butanol, or mixtures thereof. A preferred organic solvent is tert-butanol.

In one embodiment of the invention are methods of preparing lyophilized compositions that comprise at least one crystalline form of bendamustine hydrochloride. Preferably, the crystalline form of bendamustine hydrochloride is bendamustine hydrochloride Form 1, bendamustine hydrochloride Form 2, bendamustine hydrochloride Form 3, bendamustine hydrochloride Form 4, or a mixture thereof. In other embodiments of the invention, the lyophilized compositions further comprise amorphous bendamustine hydrochloride. More preferred methods of the invention produce lyophilized compositions comprising a mixture of bendamustine Form 4 and amorphous bendamustine hydrochloride.

Preferred methods of preparing lyophilized compositions comprising at least one crystalline form of bendamustine hydrochloride comprise combining bendamustine hydrochloride with at least one solvent to form a solution and then lyophilizing the solution. In some embodiments, the solution further comprises at least one lyophilization excipient. Preferred lyophilization excipients include, for example, sodium phosphate, potassium phosphate, citric acid, tartaric acid, gelatin, glycine, mannitol, lactose, sucrose, maltose, glycerin, dextrose, dextran, trehalose, hetastarch, or a mixture thereof. More preferably, the pharmaceutically acceptable excipient is mannitol. In some embodiments, the solvent is water, an organic solvent, or a mixture thereof. Preferably, the organic solvent is methanol, ethanol, n-propanol, iso-propanol, n-butanol, tert-butanol, or a mixture thereof. More preferably, the organic solvent is tert-butanol. In certain embodiments, the solvent is a mixture of water and an organic solvent, for example, a mixture having a ratio of water to organic solvent of from about 1:1 to about 3:1 (v/v), preferably about 7:3 (v/v).

Figure 14:
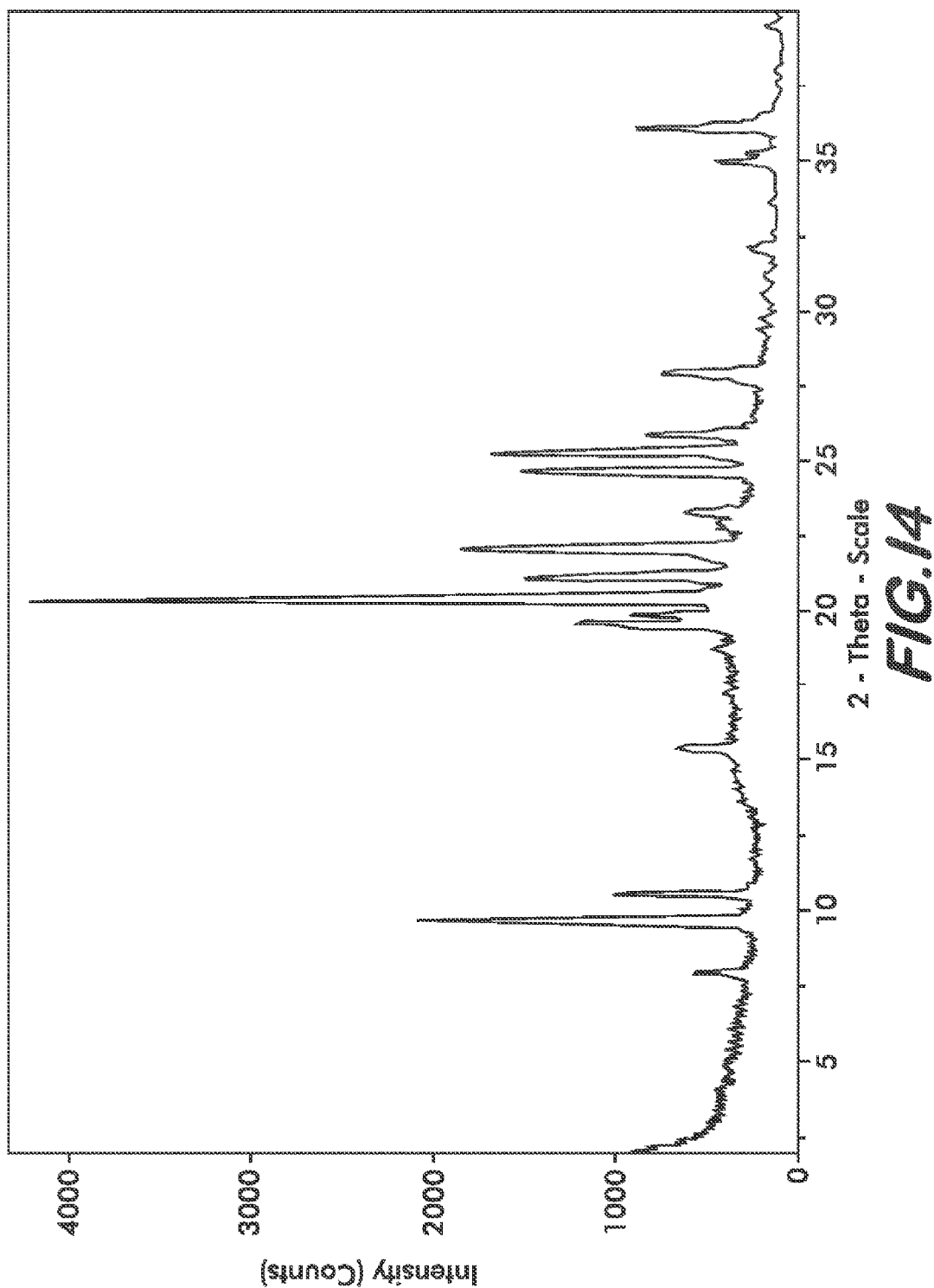
FIG. 14 is an X-ray Powder Diffractogram of one embodiment of the present invention comprising amorphous bendamustine hydrochloride, bendamustine hydrochloride Form 3, and mannitol (Lot#426804).

Lyophilized compositions produced according to any of the methods described herein are also within the scope of the invention. An X-ray Powder Diffractogram of one such composition, prepared in accordance with the lyophilization procedures described herein and comprising amorphous bendamustine hydrochloride, bendamustine hydrochloride Form 3, and mannitol is shown in FIG. 14. The XPRD data corresponding to this Diffractogram is shown below.

| Angle (2-Theta) | d value (Angstrom) | Intensity (Counts) | Intensity (%) |
|---|---|---|---|
| 7.98 | 11.07642 | 231 | 6.3 |
| 9.75 | 9.06671 | 1710 | 47.0 |
| 10.58 | 8.35697 | 751 | 20.7 |
| 13.68 | 6.46585 | 30 | 0.8 |
| 15.43 | 5.73932 | 286 | 7.9 |
| 18.69 | 4.74293 | 91 | 2.5 |
| 19.48 | 4.55224 | 474 | 13.1 |
| 19.64 | 4.51705 | 799 | 22.0 |
| 19.89 | 4.45920 | 416 | 11.5 |
| 20.45 | 4.33901 | 3635 | 100.0 |
| 21.12 | 4.20296 | 1052 | 29.0 |
| 21.30 | 4.16740 | 545 | 15.0 |
| 22.15 | 4.01060 | 1349 | 37.1 |
| 22.76 | 3.90380 | 95 | 2.6 |
| 23.34 | 3.80874 | 293 | 8.1 |
| 24.72 | 3.59834 | 1153 | 31.7 |
| 25.30 | 3.51781 | 1396 | 38.4 |
| 25.43 | 3.50023 | 899 | 24.7 |
| 25.91 | 3.43569 | 454 | 12.5 |
| 27.95 | 3.19006 | 534 | 14.7 |
| 29.39 | 3.03627 | 35 | 1.0 |
| 29.73 | 3.00276 | 40 | 1.1 |
| 30.64 | 2.91594 | 38 | 1.1 |
| 31.20 | 2.86471 | 39 | 1.1 |
| 32.22 | 2.77642 | 109 | 3.0 |
| 33.65 | 2.66154 | 37 | 1.0 |
| 35.00 | 2.56159 | 287 | 7.9 |
| 35.34 | 2.53782 | 117 | 3.2 |
| 36.11 | 2.48539 | 682 | 18.8 |
| 36.23 | 2.47719 | 538 | 14.8 |
| 36.58 | 2.45430 | 105 | 2.9 |
| 38.04 | 2.36363 | 27 | 0.8 |
| 39.53 | 2.27806 | 36 | 1.0 |

Also within the scope of the invention are methods of treating diseases, such as, for example, chronic lymphocytic leukemia, Hodgkin's disease, non-Hodgkin's lymphoma, multiple myeloma, or breast cancer, with a pharmaceutical composition of the present invention. Preferably, the solid forms of the invention are used to treat chronic lymphocytic leukemia. Also preferred are methods of using the solid forms of the invention to treat indolent B-cell non-Hodgkin's lymphoma, in particular, indolent B-cell non-Hodgkin's lymphoma that has progressed during or within six months of treatment with, for example, rituximab or a rituximab-containing regimen. In certain embodiments, the method comprises administering a therapeutically effective amount of a pharmaceutical composition of the present invention directly to the patient (for example, when the pharmaceutical composition is a tablet or capsule). In other embodiments, the method comprises modifying a pharmaceutical composition of the present invention before administration, such as by dissolving the composition in water or another solvent prior to administration. In these embodiments, the method comprises administering to the patient a therapeutically effective amount of a preparation prepared from a pharmaceutical composition of the present invention. Preferably, the preparation is an injectable preparation. The injectable preparation may be administered subcutaneously, intracutaneously, intravenously, intramuscularly, intra-articularly, intrasynovially, intrasternally, intrathecally, intralesionally, intracranially or via infusion. Other conditions amenable to treatment utilizing the compositions and injectable preparations of the present invention include small cell lung cancer, hyperproliferative disorders, and autoimmune diseases, such as rheumatoid arthritis, multiple sclerosis, and lupus.

Preferably, the dose administered is about 100 mg/m$^2$ or about 120 mg/m$^2$, administered intravenously. Dosages of about 25 mg/m$^2$, 60 mg/m$^2$, 50 mg/m$^2$ and 90 mg/m$^2$, administered intravenously, are also within the scope of the invention. Preferably, the dosage is administered intravenously over about 30 minutes or over about 60 minutes. Also preferred are methods of administration wherein the dosage is administered on days 1 and 2 of a 28-day cycle. In some embodiments, the dosage is administered in from 1 to 6 or from 1 to 8 cycles.

The injectable preparations described herein are in the form of a sterile injectable preparation, for example, as a sterile, injectable aqueous or oleaginous suspension or solution formulated according to techniques known in the art. Typically, the pharmaceutical compositions of the present invention, containing at least one of Form 1, Form 2, Form 3, Form 4, or amorphous bendamustine hydrochloride, preferably at least one of Form 1, Form 3, Form 4, or amorphous bendamustine hydrochloride, are formulated as lyophilized powders which may be provided, for example, in vials containing 100 mg of drug per 50 mL or 20 mL vial. The injectable preparation may be prepared by reconstitution of a freeze-dried or lyophilized composition with Sterile Water for Injection and then further dilution with a pharmaceutically acceptable intravenous solution, such as, for example, 0.9% sodium Chloride, 5% dextrose in water (D5W), Lactated Ringers solution, or 0.45% Sodium Chloride/2.5% dextrose.

Preferably, the pharmaceutical compositions of bendamustine hydrochloride described herein are reconstituted into an injectable preparation, for example, with sterile water, in less than about 20 minutes. More preferably, reconstitution occurs in less than about 10 minutes, most preferably about 5 minutes.

A typical reconstitution process would include reconstituting, preferably aseptically, 100 mg bendamustine hydrochloride with 20 mL Sterile Water for Injection. This yields a clear, colorless to pale yellow solution having a bendamustine HCl concentration of 5 mg/mL. If lyophilized bendamustine hydrochloride is being reconstituted, the bendamustine hydrochloride should completely dissolve in about 5 minutes. The volume needed for the required dose (based on 5 mg/mL concentration) can be aseptically withdrawn and transferred to a 500 mL infusion bag of 0.9% Sodium Chloride (or other pharmaceutically acceptable intravenous solution) for injection. Preferably, the reconstituted solution is transferred to the infusion bag within 30 minutes of reconstitution. After transfer, the contents of the infusion bag are thoroughly mixed. Administration by intravenous infusion is typically provided over a time period of from about 30 to about 60 minutes.

It is envisioned that the pharmaceutical compositions of the present invention can be administered in combination with one or more anti-neoplastic agents where the anti-neoplastic agent is given prior to, concurrently with, or subsequent to the administration of the composition of the present invention. Pharmaceutically acceptable anti-neoplastic agents are known in the art. Preferred anti-neoplastic agents are those disclosed in co-pending U.S. application Ser. No. 11/330, 868, filed Jan. 12, 2006, the entirety of which is incorporated herein by reference.

Therapeutically effective amounts of bendamustine can be readily determined by an attending diagnostician by use of conventional techniques. The effective dose can vary depending upon a number of factors, including type and extent of progression of the disease or disorder, overall health of a particular patient, biological efficacy of bendamustine, formulation of bendamustine, and route of administration of the forms of bendamustine. Bendamustine can also be administered at lower dosage levels with gradual increases until the desired effect is achieved.

TERMINOLOGY

The term "anti-solvent," as used herein, means a solvent in which a compound is substantially insoluble.

The term "crystalline," as used herein, means having a regularly repeating arrangement of molecules or external face planes.

The term "crystalline composition," as used in herein, refers to a solid chemical compound or mixture of compounds that provides a characteristic pattern of peaks when analyzed by x-ray powder diffraction; this includes, but is not limited to, polymorphs, solvates, hydrates, co-crystals, and desolvated solvates.

The term "isolating" as used herein, means separating a compound from a solvent, anti-solvent, or a mixture of solvent and anti-solvent to provide a solid, semisolid or syrup. This is typically accomplished by means such as centrifugation, filtration with or without vacuum, filtration under positive pressure, distillation, evaporation or a combination thereof. Isolating may or may not be accompanied by purifying during which the chemical, chiral or chemical and chiral purity of the isolate is increased. Purifying is typically conducted by means such as crystallization, distillation, extraction, filtration through acidic, basic or neutral alumina, filtration through acidic, basic or neutral charcoal, column chromatography on a column packed with a chiral stationary phase, filtration through a porous paper, plastic or glass barrier, column chromatography on silica gel, ion exchange chromatography, recrystallization, normal-phase high performance liquid chromatography, reverse-phase high performance liquid chromatography, trituration and the like.

The term "pharmaceutically acceptable excipient," as used herein, includes any and all solvents, dispersion media, coatings, antibacterial and antifungal agents, isotonic and absorption delaying agents and the like. The use of such media and agents for pharmaceutical active substances is well known in the art, such as in *Remington: The Science and Practice of Pharmacy*, 20$^{th}$ ed.; Gennaro, A. R., Ed.; Lippincott Williams & Wilkins: Philadelphia, Pa., 2000. Except insofar as any conventional media or agent is incompatible with the active ingredient, its use in the therapeutic compositions is contemplated. Supplementary active ingredients can also be incorporated into the compositions.

The term "solution," as used herein, refers to a mixture containing at least one solvent and at least one compound that is at least partially dissolved in the solvent.

The term "solvate," as used herein, means a crystalline composition of variable stoichiometry formed by a solute and an organic solvent as defined herein.

The term "solvent," as used herein, means a substance, typically a liquid, that is capable of completely or partially dissolving another substance, typically a solid. Solvents for the practice of this invention include, but are not limited to, water, acetic acid, acetone, acetonitrile, benzene, chloroform, carbon tetrachloride, dichloromethane, dimethylsulfoxide, 1,4-dioxane, ethanol, ethyl acetate, butanol, tert-butanol, N,N-dimethylacetamide, N,N-dimethylformamide, formamide, formic acid, heptane, hexane, isopropanol, methanol, methyl ethyl ketone (butanone), 1-methyl-2-pyrrolidinone, mesitylene, nitromethane, polyethylene glycol, propanol, 2-propanone, propionitrile, pyridine, tetrahydrofuran, toluene, xylene, mixtures thereof and the like.

The term "sublimation," as used herein, refers to the transition from the solid phase to the gas phase with no intermediate liquid stage.

The term "substantially free," as used herein with regard to compositions that contain a particular form of bendamustine hydrochloride while being "substantially free" of other forms of the compound, means that the recited form is associated with less than 10%, preferably less than 5%, in particular less than 2% and most preferably less than 1% of the other recited forms of bendamustine hydrochloride.

The term "therapeutically effective amount," as used herein, refers to the amount determined to be required to produce the physiological effect intended and associated with a given drug, as measured according to established pharmacokinetic methods and techniques, for the given administration route. Appropriate and specific therapeutically effective amounts can be readily determined by the attending diagnostician, as one skilled in the art, by the use of conventional techniques. The effective dose will vary depending upon a number of factors, including the type and extent of progression of the disease or disorder, the overall health status of the particular patient, the relative biological efficacy of the compound selected, the formulation of the active agent with appropriate excipients, and the route of administration.

Instrumentation

X-Ray Powder Diffraction (XRPD)

The novel crystalline forms of bendamustine hydrochloride have been characterized by XRPD which produces a fingerprint of the particular crystallite form. Measurements of 2θ values typically are accurate to within ±0.2 degrees.

Bruker AXS/Diemens D5000

X-Ray Powder Diffraction patterns were collected on a Siemens D5000 diffractometer using CuKα radiation (40 kV, 40 mA), θ-θ goniometer, automatic divergence and receiving slits, a graphite secondary monochromator and a scintillation counter. The instrument is performance checked using a certified corundum standard (NIST 1976).

Ambient Conditions—

Samples run under ambient conditions were prepared as flat plate specimens. Approximately 35 mg of the sample was gently packed into a cavity cut into polished, zero-background (510) silicon wafer and a Mylar cover was placed over the sample. The sample was rotated in its own plane during analysis.

Bruker AXS C2 GADDS

X-Ray Powder Diffraction patterns were collected on a Bruker AXS C2 GADDS diffractometer using Cu Kα radiation (40 kV, 40 mA), automated XYZ stage, laser video microscope for autosample positioning and a HiStar 2-dimensional area detector. X-ray optics consists of a single Göbel multilayer mirror coupled with a pinhole collimator of 0.3 mm.

The beam divergence, i.e. the effective size of the X-ray beam on the sample, was approximately 5 mm. A θ-θ continuous scan mode was employed with a sample—detector distance of 20 cm which gives an effective 2θ range of 3.2°-29.7°. Typically, the sample would be exposed to the X-ray beam for 120 seconds.

Ambient Conditions—

Samples run under ambient conditions were prepared as flat plate specimens using powder without grinding. Approximately 1-2 mg of the sample was lightly pressed on a glass slide to obtain a flat surface.

Non-Ambient Conditions—

Samples run under non-ambient conditions were mounted on a silicon wafer with heatconducting compound. The sample was then heated to the appropriate temperature at ca. 20° C. min$^{-1}$ and subsequently held isothermally for ca 1 minute before data collection was initiated.

Single Crystal X-Ray Diffraction (SCXRD)

The crystals chosen were coated with paratone oil and flash frozen on a (Bruker SMART CCD diffractometer. Data were collected on a Bruker AXS 1K SMART CCD diffractometer equipped with an Oxford Cryosystems Cryostream cooling device. Structures were solved using either the SHELXS or SHELXD programs and refined with the SHELXL program as part of the Bruker AXS SHELXTL suite. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

$^1$H NMR $^1$H NMR spectra were collected on a Bruker 400 MHz instrument equipped with an auto-sampler and controlled by a DRX400 console. Automated experiments were acquired using ICON-NMR v4.0.4 (build 1) running with Topspin v 1.3 (patch level 6) using the standard Bruker loaded experiments. For non-routine spectroscopy, data were acquired through the use of Topspin alone. Samples were prepared in d6-DMSO, unless otherwise stated. Off-line analysis was carried out using ACD SpecManager v 9.09 (build 7703).

Differential Scanning Calorimetry (DSC)

DSC data were collected on a TA Instruments Q1000 equipped with a 50 position auto-sampler. The instrument was calibrated for energy and temperature calibration using certified indium. Typically 0.5-2 mg of each sample, in a pin-holed hermetically sealed aluminium pan, was heated at 10° C.·min-1 from 25° C. to 200° C. A nitrogen purge at 50 ml·min-1 was maintained over the sample. The instrument control software was Thermal Advantage v4.6.6 and the data were analyzed using Universal Analysis v4.3A.

Thermo-Gravimetric Analysis (TGA)

TGA data were collected on a TA Instruments Q500 TGA, equipped with a 16 position autosampler. The instrument was temperature calibrated using certified Alumel. Typically 1-2 mg of each sample was loaded into a pin-holed hermetically sealed aluminum DSC pan on a pre-tared platinum crucible, and was heated at 10° C.·min$^{-1}$ from ambient temperature to 200° C. A nitrogen purge at 60 ml·min$^{-1}$ was maintained over the sample. The instrument control software was Thermal Advantage v4.6.6 and the data were analyzed using Universal Analysis v4.3A.

Purity Analysis

Purity analysis was performed on an Agilent HP1100 series system equipped with a diode array detector and using ChemStation software vB.02.01-SR1.

| | Type of method | | |
|---|---|---|---|
| | Normal Phase | Reverse Phase | ✓ |
| | Isocratic | Gradient | ✓ |
| Column: | Zorbax Bonus-RP C14, 150 × 4.6 mm, 5 µm | | |
| Column Temperature (° C.): | 30 | | |
| Test Sample Make-Up: | NMP/mobile phase A 1:1 | | |
| Injection (µl): | 2 | | |
| Detection: Wavelength, Bandwidth(nm): | 254, 8 | | |

| | | | |
|---|---|---|---|
| Flow Rate (ml · min–1): | 1.0 | | |
| Phase A: | 0.1% TFA in water | | |
| Phase B: | 0.1% TFA in acetonitrile | | |
| Timetable: | Time (min) | % Phase A | % Phase B |
| | 0 | 93 | 7 |
| | 5 | 93 | 7 |
| | 13 | 73 | 27 |
| | 16 | 73 | 27 |
| | 25 | 43 | 57 |
| | 26 | 10 | 90 |
| | 31 | 10 | 90 |

Thermodynamic Aqueous Solubility by HPLC

Aqueous solubility was determined by suspending sufficient compound in 0.25 ml of water to give a maximum final concentration of ≥10 mg·ml$^{-1}$ of the parent free-form of the compound. The suspension was equilibrated at 25° C. for 24 hours (unless otherwise stated) after which the pH was measured. The suspension was then filtered through a glass fibre C filter into a 96 well plate. The filtrate was then diluted by a factor of 100 times. Quantitation was by HPLC with reference to a standard solution of approximately 0.1 mg·ml-1 in DMSO. Different volumes of the standard, diluted and undiluted sample solutions were injected. The solubility was calculated using the peak areas determined by integration of the peak found at the same retention time as the principal peak in the standard injection.

| | | | |
|---|---|---|---|
| Type of method: | Reverse phase with gradient elution | | |
| Column: | Phenomenex Luna, C18 (2) 5 µm 50 × 4.6 mm | | |
| Column Temperature (° C.): | 25 | | |
| Injection (µl): | 5, 8 and 50 | | |
| Type of method: | Reverse phase with gradient elution | | |
| Detection: Wavelength, Bandwidth (nm): | 260, 80 | | |
| Flow Rate (ml · min–1): | 2 | | |
| Phase A: | 0.1% TFA in water | | |
| Phase B: | 0.085% TFA in acetonitrile | | |
| Timetable: | Time (min) | % Phase A | % Phase B |
| | 0.0 | 95 | 5 |
| | 1.0 | 80 | 20 |
| | 2.3 | 5 | 95 |
| | 3.3 | 5 | 95 |
| | 3.5 | 95 | 5 |
| | 4.4 | 95 | 5 |

Gravimetric Vapor Sorption (GVS)

Sorption isotherms were obtained using a Hiden IGASorp moisture sorption analyser, controlled by CFRSorp software. The sample temperature was maintained at 25° C. by a Huber recirculating water bath. The humidity was controlled by mixing streams of dry and wet nitrogen, with a total flow rate of 250 ml·min-1. The relative humidity was measured by a calibrated Vaisala RH probe (dynamic range of 0-95% RH), located near the sample. The weight change, (mass relaxation) of the sample as a function of % RH was constantly monitored by themicrobalance (accuracy ±0.001 mg). Typically 1-3 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0-90% RH range.

| Parameter | Values |
| --- | --- |
| Adsorption -Scan 1 | 40-90 |
| Desorption/Adsorption -Scan 2 | 85 -Dry, Dry -40 |
| Intervals (% RH) | 10 |
| Number of Scans | 2 |
| Flow rate (ml · min$^{-1}$) | 250 |
| Temperature (° C.) | 25 |
| Stability (° C. · min$^{-1}$) | 0.05 |
| Minimum Sorption Time (hours) | 1 |
| Maximum Sorption Time (hours) | 4 |
| Mode | AF2 |
| Accuracy (%) | 98 |

The software uses a least squares minimization procedure together with a model of the mass relaxation, to predict an asymptotic value. The measured mass relaxation value must be within 5% of that predicted by the software before the next % RH value is selected. The minimum equilibration time was set to 1 hour and the maximum to 4 hours.

pKa Determination and Prediction

Data were collected on a Sirius GlpKa instrument with a D-PAS attachment. Measurements were made at 25° C. in aqueous solution by UV. The compound was initially dissolved in DMSO at 5 mg/ml of which 50 μl (0.25 mg) was used for the titration from pH 1.3 to 9.0. The titration media was ionic-strength adjusted (ISA) with 0.15 M KCl (aq). The data were refined using Refinement Pro software v1.0. Prediction of pKa values was made using ACD pKa prediction software v9.

Log P Determination

Data were collected by potentiometric titration on a Sirius GlpKa instrument using three ratios of octanol:ionic-strength adjusted (ISA) water to generate Log P, Log Pion, and Log D values. The data were refined using Refinement Pro software v1.0. Prediction of Log P values was made using ACD v9 and Syracuse KOWWIN v1.67 software.

Preparation of Bendamustine Hydrochloride (Crude)

Step 1:

4-{5-[Bis-(2-hydroxy-ethyl)-amino]-1-methyl-1H-benzoimidazol-2-yl}-butyric acid ethyl ester (27.0 kg) was dissolved in 270 kg chloroform. After cooling to 0 to 5° C., 19.2 kg thionyl chloride was added over about 1 hour. The mixture was warmed to 25° C.±5° C. and stirred for 20 to 24 hours. 75.6 kg hydrochloric acid (32% aqueous solution) was then added. After phase separation, the organic (lower) phase was removed. The product remained in the aqueous phase.

Step 2:

A suspension of activated charcoal in hydrochloric acid was added to the aqueous phase obtained in step 1. The mixture was heated over 1 hour to 85 to 90° C. and stirred for 4 to 5 hours at reflux. The suspension was then filtered and rinsed with aqueous hydrochloric acid. The solvent was distilled off under reduced pressure at a temperature not exceeding 65° C. 108 kg to 324 kg (108 kg preferred) of warm (35 to 45° C.) deionized water was added to induce crystallization.

After crystallization, the mixture was cooled to 20 C±5° C. and stirred for an additional 1 to 2 hours or overnight. The product was collected by filtration on a filter dryer, washed with three portions each of 108 to 324 kg (108 kg preferred) deionized water and 108 to 216 kg (108 kg preferred) of cold acetone. The crude product was treated four times each with 54 to 108 kg (54 kg preferred) acetone at reflux for at least 1 hour, in the filter dryer. The suspension was filtered and the product dried at a temperature not higher than 40° C. under reduced pressure, to give 21.4 kg±2.1 kg bendamustine hydrochloride crude (70%±10%, calculated as dried substance).

Step 3 (Optional):

The product obtained from step 2 was dissolved in hydrochloric acid (32% aqueous solution) and heated to reflux (85 to 90° C.) for at least 4 hours. To improve color, activated charcoal can be added to the hydrochloric acid and the mixture heated to reflux (85 to 90° C.) for at least 4 hours. With activated charcoal, the suspension was filtered and rinsed with aqueous hydrochloric acid. Solvent was distilled off under reduced pressure at a temperature not exceeding 65° C. The mixture was then diluted with deionized water. If no crystallization occurred within 15 min, the mixture was seeded. After crystallization, the suspension was stirred at 40° C.±5° C. for one hour, then cooled to 20° C.±5° C. After stirring an additional 1 to 2 hours at 20° C.±5° C., the product was collected by filtration, washed three times with cold deionized water, and at least three times with cold acetone. The crude product was treated four times with acetone at reflux for at least 1 hour. The suspension was filtered and the product dried at a temperature not higher than 40° C., under reduced pressure. Yield was of crude bendamustine hydrochloride was 80%±10%.

Preparation of Purified Bendamustine Hydrochloride

Bendamustine HCl crude (15.0 kg) was suspended with 0.45 kg activated charcoal in ethanol/water (vol/vol=97/3) at room temperature. The mixture was quickly warmed to 75 to 80° C. and stirred for not more than 10 min under reflux conditions. The mixture was filtered to remove the activated charcoal. After filtration, 33.0 kg of filtered acetone was added quickly at 40-50° C. to induce crystallization.

After crystallization, the mixture was stirred for 30 to 60 min at 40-50° C., then cooled to 0 to 5° C., and stirred for at least an additional 30 min or overnight. The product was collected by filtration and washed with three 45 kg of cold acetone. After that, the crude product was treated 4 times each with 30 kg acetone at reflux for at least 1 hour. The suspension was filtered and the product dried at a temperature not higher than 40° C. under reduced pressure providing 11.3±1.5 kg bendamustine hydrochloride (75%±10%).

Preparation of Bulk Solution (1 L) of Bendamustine Hydrochloride

Under sterile conditions, Water for Injection ("WFI," ~65% of total batch size) was transferred to a stainless steel compounding vessel equipped with a mixer. The temperature of the WFI in the compounding tank was adjusted to 15 to 25° C. Mannitol (25.5 g) was added to the compounding vessel and mixed at for a minimum of 5 minutes while maintaining the solution temperature at 15 to 25° C. Tertiary butyl alcohol ("TBA," 234.2 g) was added to the compounding vessel. The solution was mixed for a minimum of minutes at 15 to 25° C. Purified bendamustine HCl (15.0 g) was added to the compounding vessel and mixed for a minimum of 10 minutes while maintaining the solution temperature between 15 to 25° C. Water for Injection, USP, sufficient to bring the batch to 1 L was added and mixed for a minimum of 10 minutes. The bulk solution was sterilized by filtration through a 0.22 μm filter using nitrogen at 1-2 bar.

Lyophilization of Filtered Bulk Solution of Bendamustine Hydrochloride

Step 1:

The formulated, sterile filtered bendamustine HCl bulk solution was filled by a fully automated filling/stoppering machine. The vials continued to the stoppering station, where they were partially stoppered with pre-sterilized stoppers. Bendamustine HCl drug product was filled to approximately 6.47 g (6.67 mL) in a 20-cc Type I borosilicate tubing glass amber vial. Filled and partially stoppered vials were transferred to the lyophilizer located in the lyophilization area.

Step 2:

The filled and partially stoppered vials from step 1 are transferred to the lyophilizer equipped with eight shelves that can be loaded with product-filled trays. The filled and partially stoppered drug product vials were lyophilized. A summary of the freeze drying cycle used during lyophilization of bendamustine HCl drug product is provided in the Table 1 below.

TABLE 1

Lyophilization Cycle for Bendamustine HCl

| Process parameters | Target Setpoint |
| --- | --- |
| Loading temperature | 5° C. |
| Freezing temperature | Hold at −50° C. for 4 hours |
| Primary drying vacuum | 150 microns |
| Primary drying temperature | Hold at −15° C. for 27 hours |
| Intermediate drying temperature | Hold at −12° C. for 7 hours |
| Secondary drying vacuum | 50 microns |
| Secondary drying temperature | Hold at 40° C. for 15 hours |

At the end of the lyophilization cycle, the chamber pressure was raised to ~0.6 bar with sterile filtered nitrogen. The vials were hydraulically stoppered by adjusting the shelves to the stoppering position under sterile filtered nitrogen atmosphere. After the vials were stoppered, the shelves were raised, and the chamber was backfilled with sterile filtered air to atmospheric pressure for unloading. This procedure results in about 100 mg of bendamustine HCl/vial.

Preparation of Solutions of Bendamustine Hydrochloride 50 mg of bendamustine hydrochloride Form 1 was weighed into a screw-top vial. Solvent was added in aliquots (with heating to 50° C.) until a clear solution was obtained. Observations are recorded in Table 2.

TABLE 2

Solubility of Bendamustine Hydrochloride

| Solvent | Volume Added | Solution Obtained? |
| --- | --- | --- |
| Ethanol | 1 ml | Yes (50° C.) |
| Acetic acid | 1 ml | Yes (50° C.) |
| Methanol | 100 µl | Yes (50° C.) |
| Formamide | 1 ml | Yes (50° C.) |
| DMF | 500 µl | Yes (50° C.) |
| DMSO | 100 µl | Yes (50° C.) |
| DMA | 500 µl | Yes (50° C.) |

Maturation Experiment

Approximately 10 mg of Form 1 bendamustine hydrochloride was slurried in the solvents list in Table 3. The slurries were shaken for 48 hours with alternating 4 hour periods at 50 C and ambient temperature. Any solid material was then isolated by filtration and analyzed by XRPD. Solutions were allowed to evaporate. Results are shown in Table 3 below.

TABLE 3

Assignment of XRPD Results from Maturation of Bendamustine Hydrochloride

| Solvent | XRPD Analysis | Solvent | XRPD Analysis |
| --- | --- | --- | --- |
| Ethanol | Form 1 | DCM | Form 1 |
| Ethyl acetate | Form 1 | | |
| TBME | Form 1 | Methyl acetate | Form 1 |

TABLE 3-continued

Assignment of XRPD Results from Maturation of Bendamustine Hydrochloride

| Solvent | XRPD Analysis | Solvent | XRPD Analysis |
| --- | --- | --- | --- |
| IPA | Form 1 | DMF | Hydrate (Form 2) |
| Isopropyl acetate | Form 1 | | |
| Acetone | Form 1 | Dioxane | Form 1 |
| THF | Form 1 | Diethyl ether | Form 1 |
| Acetonitrile | Form 1 | Anisole | Form 1 |
| Heptane | Form 1 | MIBK | Form 1 |
| Water | degradant | Nitromethane | Form 1 |
| Toluene | Form 1 | DIPE | Form 1 |
| Methanol | Mix of Form 1 and hydrate (Form 2) | DMA | Hydrate (Form 2) |

Crystallization of Bendamustine by Fast Evaporation

Solutions of Bendamustine Hydrochloride in ethanol, acetic acid, methanol, formamide, DMF, DMSO, and DMA were allowed to evaporate under ambient conditions by allowing the uncapped vials of solution to evaporate to dryness (referred to herein as "rapid evaporation"). Resulting solids were analyzed by XRPD. Results are shown in Table 4.

TABLE 4

Assignment of XRPD Results from Crystallization of Bendamustine Hydrochloride by Fast Evaporation

| Solvent | XRPD Analysis |
| --- | --- |
| Ethanol | Form 1 |
| Acetic acid | Hydrate (Form 2) |
| Methanol | Mix of Form 1 and hydrate (Form 2) |
| DMF | Form 1 |
| DMSO | Form 1 |
| DMA | Form 1 |

Crystallization of Bendamustine by Slow Evaporation

Solutions of Bendamustine Hydrochloride in ethanol, acetic acid, methanol, formamide, DMF, DMSO, and DMA were allowed to evaporate under ambient conditions by allowing the capped vials of solution, the vial caps having pinholes, to evaporate to dryness under ambient conditions. The rate of evaporation was constrained by use of air tight film covers containing small holes. Resulting solids were analyzed by XRPD. Results are shown in Table 5.

TABLE 5

Assignment of XRPD Results from Crystallization of Bendamustine Hydrochloride

| Solvent | XRPD Analysis |
| --- | --- |
| Ethanol | Form 1 |
| Acetic acid | Form 1 |
| Methanol | Mix of Form 1 and hydrate (Form 2) |
| Formamide | No solid obtained |
| DMF | Insufficient material |
| DMSO | Form 1* |
| DMA | No solid obtained |

*Single crystal data presented herein for Form 1 was obtained from a sample recrystallized from DMSO Crystallization by Anti-Solvent Toluene was added as anti-solvent to solutions of Bendamustine Hydrochloride in ethanol, acetic acid, methanol, formamide, DMF, DMSO, and DMA to encourage crystallization The volume of toluene added and observations on anti-solvent addition are recorded in Table 6. Solids were isolated by filtration. The Resulting solids were analyzed by XRPD. Results are shown in Table 6.

TABLE 6

Assignment of XRPD Results from Crystallization of Bendamustine Hydrochloride by Anti-Solvent Addition

| Solvent | Anti-Solvent Used | Volume of Anti-solvent | Observations | XRPD Analysis |
|---|---|---|---|---|
| Ethanol | Toluene | 10 ml | No precipitate - evaporated | Form 1 |
| Acetic acid | Toluene | 0.5 ml | Precipitate | Form 1 |
| DMF | Toluene | 0.5 ml | Precipitate | Form 1 |
| DMSO | Toluene | 1 ml | Precipitate | Form 1 |
| DMA | Toluene | 0.5 ml | Precipitate | Form 1 |

Preparation of Form 2 from Form 1 of Bendamustine Hydrochloride

One mL of water was added 30 mg of bendamustine hydrochloride Form 1 and the mixture warmed to 25° C. to provide a clear solution. After about 4 minutes, Form 2 precipitated from solution as a white solid. The solid was collected by filtration.

Stability of Forms 1 and 2 of Bendamustine Hydrochloride 10 mg of bendamustine hydrochloride Form 1 (A), bendamustine hydrochloride Form 2 (B), and a 1:1 mixture of Forms 1 and 2 (C) were stored under the conditions listed in Table 7. Samples were analyzed by XRPD at 1 day, 2 week, and 6 week time points. The results are shown in Table 7A. Under high humidity conditions (~90% RH), conversion of Form 1 of bendamustine hydrochloride to Form 2 was observed. The rate of this conversion appears to increase with temperature. The purity of Forms 1 and 2 after storage at 4° C./87% RH (5) and 60° C./75% RH (13) for 6 weeks was measured. No large purity decreases were observed.

TABLE 7

Bendamustine Hydrochloride Stability Study Conditions

| Condition | Temperature (° C.) | Relative Humidity (% RH) |
|---|---|---|
| 1 | 4 | 33.6 (Magnesium Chloride) |
| 2 | 4 | 43.1 (Potassium Carbonate) |
| 3 | 4 | 58.9 (Magnesium Nitrate) |
| 4 | 4 | 75.7 (Sodium Chloride) |
| 5 | 4 | 87.7 (Potassium Chloride) |
| 6 | 25 | 43.2 (Potassium Carbonate) |
| 7 | 25 | 57.6 (Sodium Bromide) |
| 8 | 25 | 75.3 (Sodium Chloride) |
| 9 | 25 | 93.6 (Potassium Nitrate) |
| 10 | 60 | 11.0 (Lithium Chloride) |
| 11 | 60 | 29.3 (Magnesium Chloride) |
| 12 | 60 | ~43 (Potassium Carbonate) |
| 13 | 60 | 74.5 (Sodium Chloride) |
| 14 | 60 | ~95 (Potassium Sulphate) |

TABLE 7A

XRPD Analysis of Stability Study Samples of Bendamustine Hydrochloride

| Condition | XRPD Analysis after 1 Day | XRPD Analysis after 2 Weeks | XRPD Analysis after 6 Weeks |
|---|---|---|---|
| 1 | No changes | No changes | No changes |
| 2 | No changes | No changes | No changes |
| 3 | No changes | No changes | No changes |
| 4 | No changes | No changes | No changes |
| 5 | No changes | C) Fully converted to Form 2 | C) Some Form 1 now present |
| 6 | No changes | No changes | No changes |
| 7 | No changes | No changes | No changes |
| 8 | No changes | No changes | No changes |
| 9 | No changes | A) Partially converted to Form 2 C) Fully converted to Form 2 | A) Partially converted to Form 2 C) Fully converted to Form 2 |
| 10 | No changes | No changes | No changes |
| 11 | No changes | No changes | No changes |
| 12 | No changes | No changes | No changes |
| 13 | Not performed | No changes | No changes |
| 14 | Not performed | A) Partially converted to Form 2 B) Sample deliquesced C) Fully converted to Form 2 | A) Fully converted to Form 2 B) Sample deliquesced C) Fully converted to Form 2 |

Light Stability of Bendamustine Hydrochloride

Samples of Form 1 and Form 2 of Bendamustine Hydrochloride were stressed in a Suntest Light Box with a light intensity of 250 watts/m2 for 1 week with the black body temperature set to 25° C. A blank of each sample, wrapped in foil for protection, was also included in the experiment. After the experiment, samples were analyzed by XRPD and the purity was determined by HPLC. A significant decrease in both crystallinity and purity was observed for Form 2 during the light stress test. In contrast, Form 1 showed only a slight decrease in purity. See Table 8.

TABLE 8

XRPD and Purity Analysis of Stability Study Samples of Bendamustine Hydrochloride

| Sample | XRPD | Purity (%) |
|---|---|---|
| Form 1 blank | No change | 97.3 |
| Form 1 | No change (sample brown in colour) | 95.9 |
| Form 2 blank | No change | 95.6 |
| Form 2 | Less crystalline (sample brown in colour) | 68.7 |

In certain embodiments, the invention is directed to a pharmaceutical composition comprising bendamustine hydrochloride Form 1, bendamustine hydrochloride Form 2, bendamustine hydrochloride Form 3, bendamustine hydrochloride Form 4, or a mixture thereof. The invention is also directed to those pharmaceutical compositions wherein the bendamustine hydrochloride is bendamustine hydrochloride Form 1. The invention is also directed to those pharmaceutical compositions wherein the bendamustine hydrochloride is bendamustine hydrochloride Form 2. The invention is also directed to those pharmaceutical compositions wherein the bendamustine hydrochloride is bendamustine hydrochloride Form 3. The invention is also directed to those pharmaceutical compositions wherein the bendamustine hydrochloride is bendamustine hydrochloride Form 4. The invention is also directed to those pharmaceutical compositions, further comprising amorphous bendamustine hydrochloride.

Other embodiments of the invention are directed to a crystalline form of bendamustine hydrochloride that is bendamustine hydrochloride Form 1, bendamustine hydrochloride Form 2, bendamustine hydrochloride Form 3, bendamustine hydrochloride Form 4, or a mixture thereof. The invention is also directed to crystalline forms, wherein the bendamustine hydrochloride is bendamustine hydrochloride Form 1 The invention is also directed to crystalline forms, wherein the bendamustine hydrochloride is bendamustine hydrochloride Form 2. The invention is also directed to crystalline forms, wherein the bendamustine hydrochloride is bendamustine hydrochloride Form 3. The invention is also directed to crystalline forms, wherein the bendamustine hydrochloride is bendamustine hydrochloride Form 4.

Figure 2:
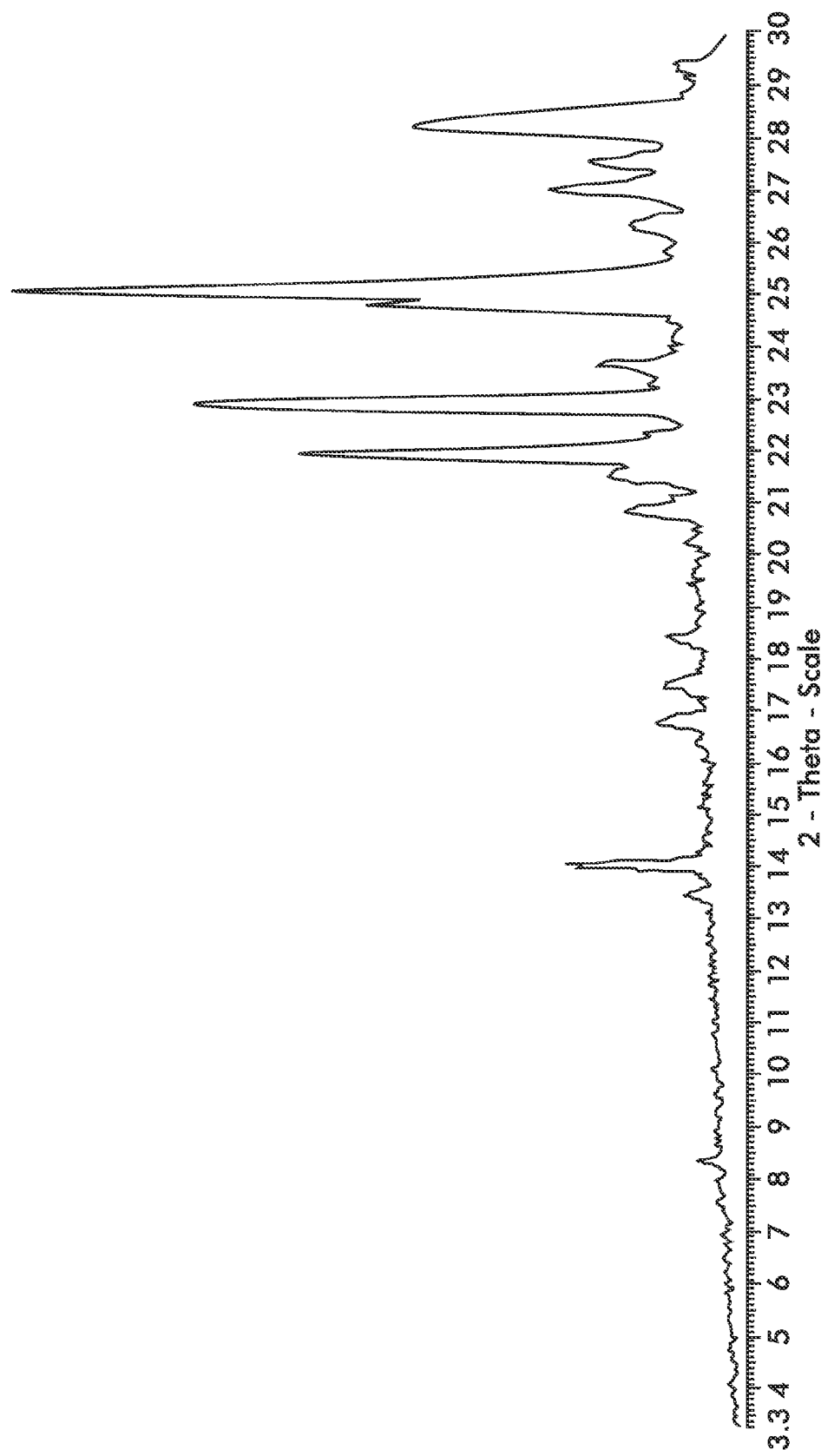
FIG. 2 is an X-ray Powder Diffractogram (XRPD) of bendamustine hydrochloride Form 1
Figure 3:
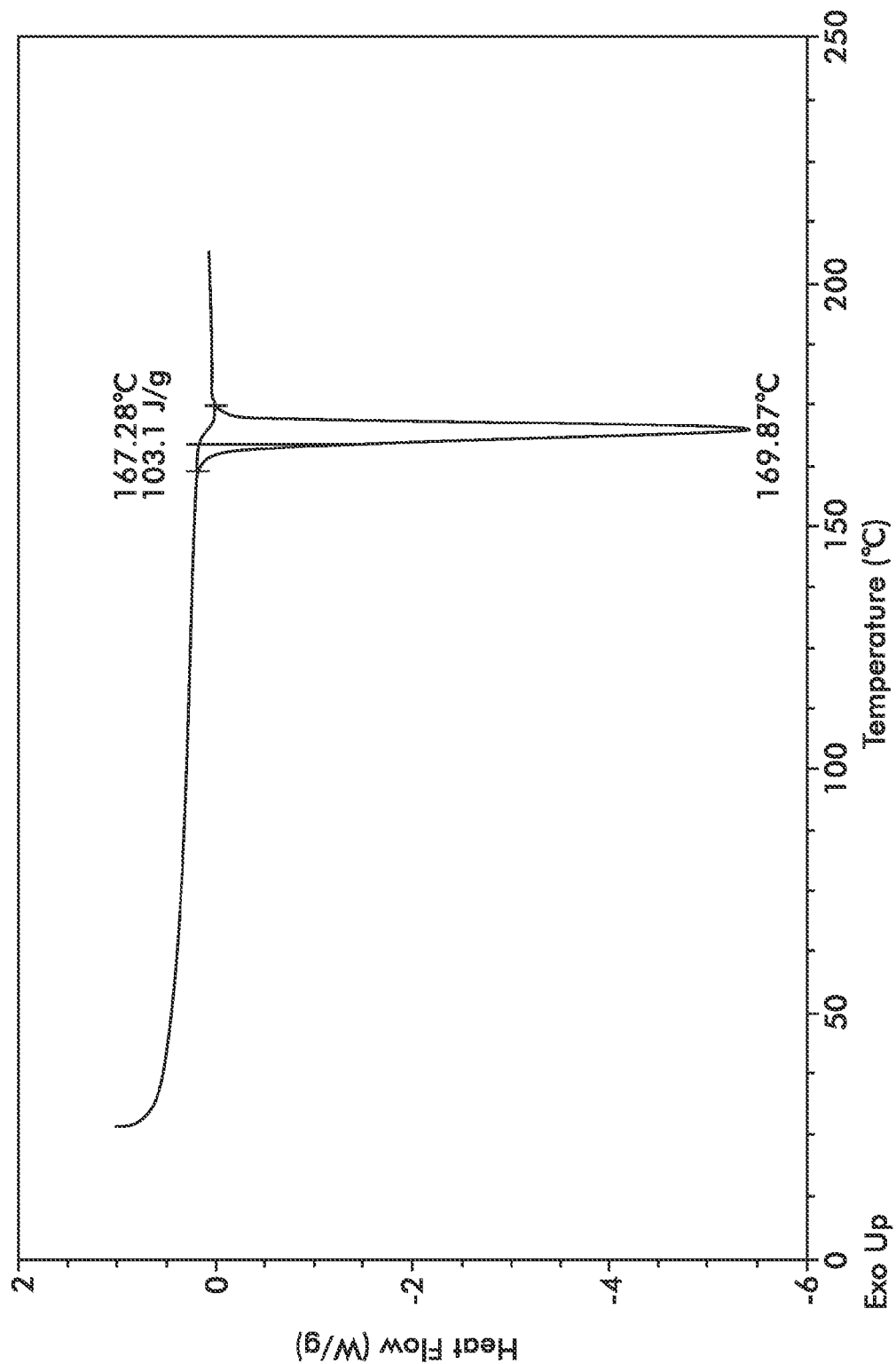
FIG. 3 is a Differential Scanning calorimetry (DSC) Thermogram of bendamustine hydrochloride Form 1
Figure 4:
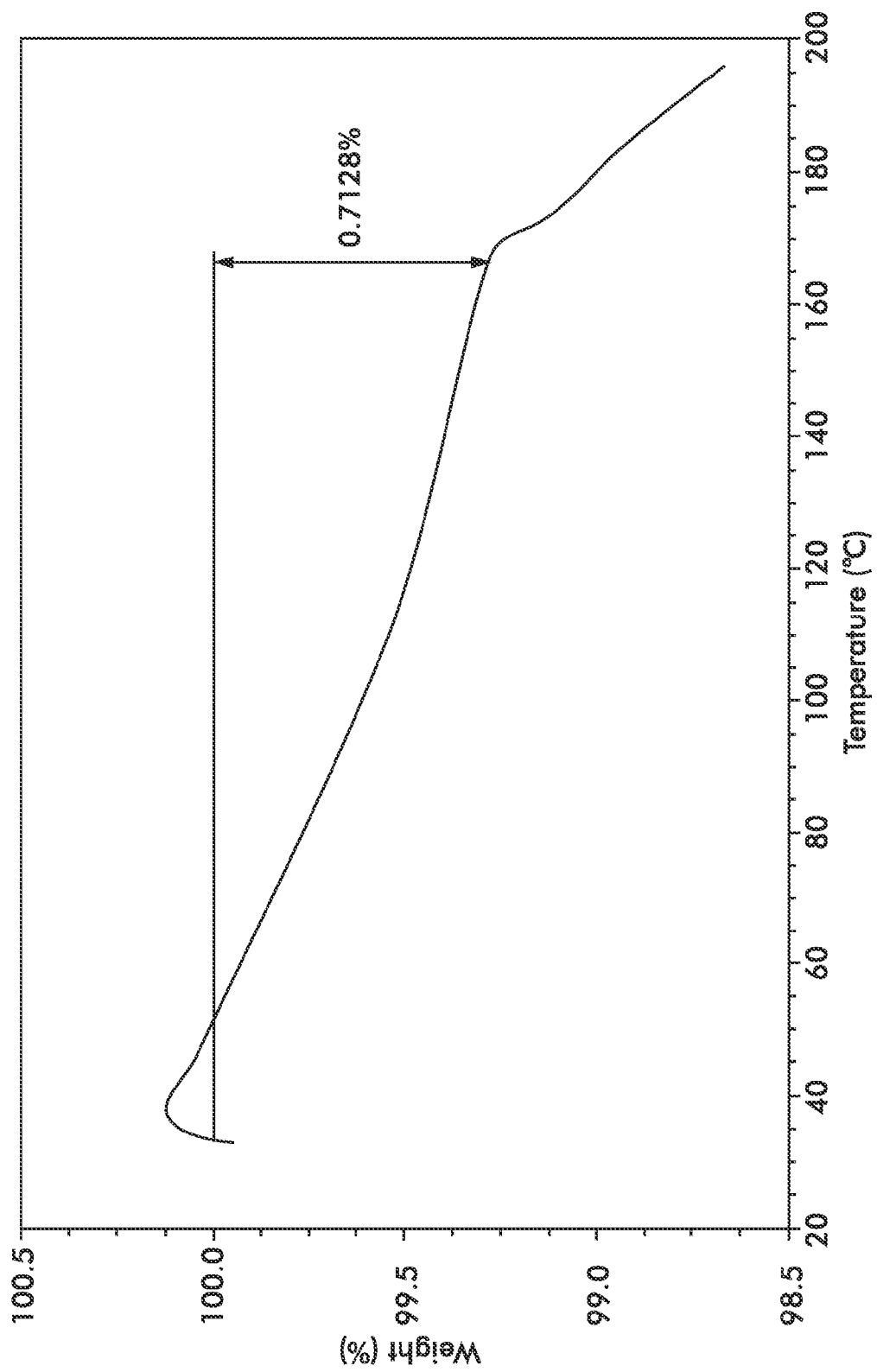
FIG. 4 is a Thermo-Gravimetric Analysis (TGA) Thermogram of bendamustine hydrochloride Form 1
Figure 5:
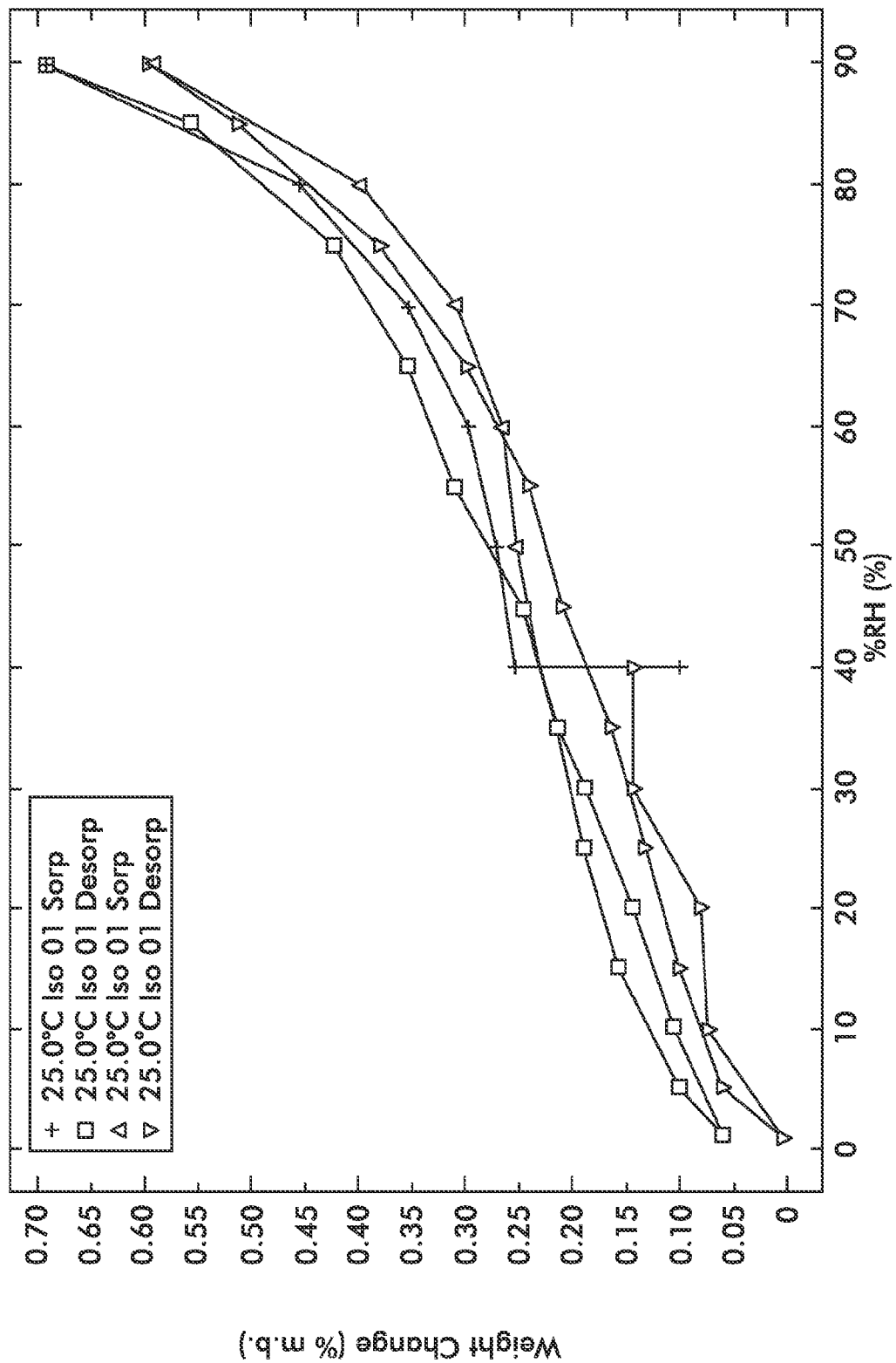
FIG. 5 is a Gravimetric Vapor Sorption (GVS) trace of bendamustine hydrochloride Form 1

Other embodiments of the invention are directed to a crystalline form of bendamustine hydrochloride that produces an X-ray powder diffraction pattern comprising one or more of the following reflections: 25.12, 24.85, 22.92, 21.97, and/or 14.05±0.2 degrees 2θ. The invention is also directed to crystalline forms of bendamustine hydrochloride that produce an X-ray powder diffraction pattern further comprising one or more of the following reflections: 16.82, 17.51, 18.45, 24.85, and/or 28.33±0.2 degrees 2θ. The invention is also directed to crystalline forms of bendamustine hydrochloride having an X-ray powder diffraction pattern substantially as depicted in FIG. 2. The invention is also directed to pharmaceutical compositions comprising the crystalline form of bendamustine hydrochloride as set forth herein.

Figure 6:
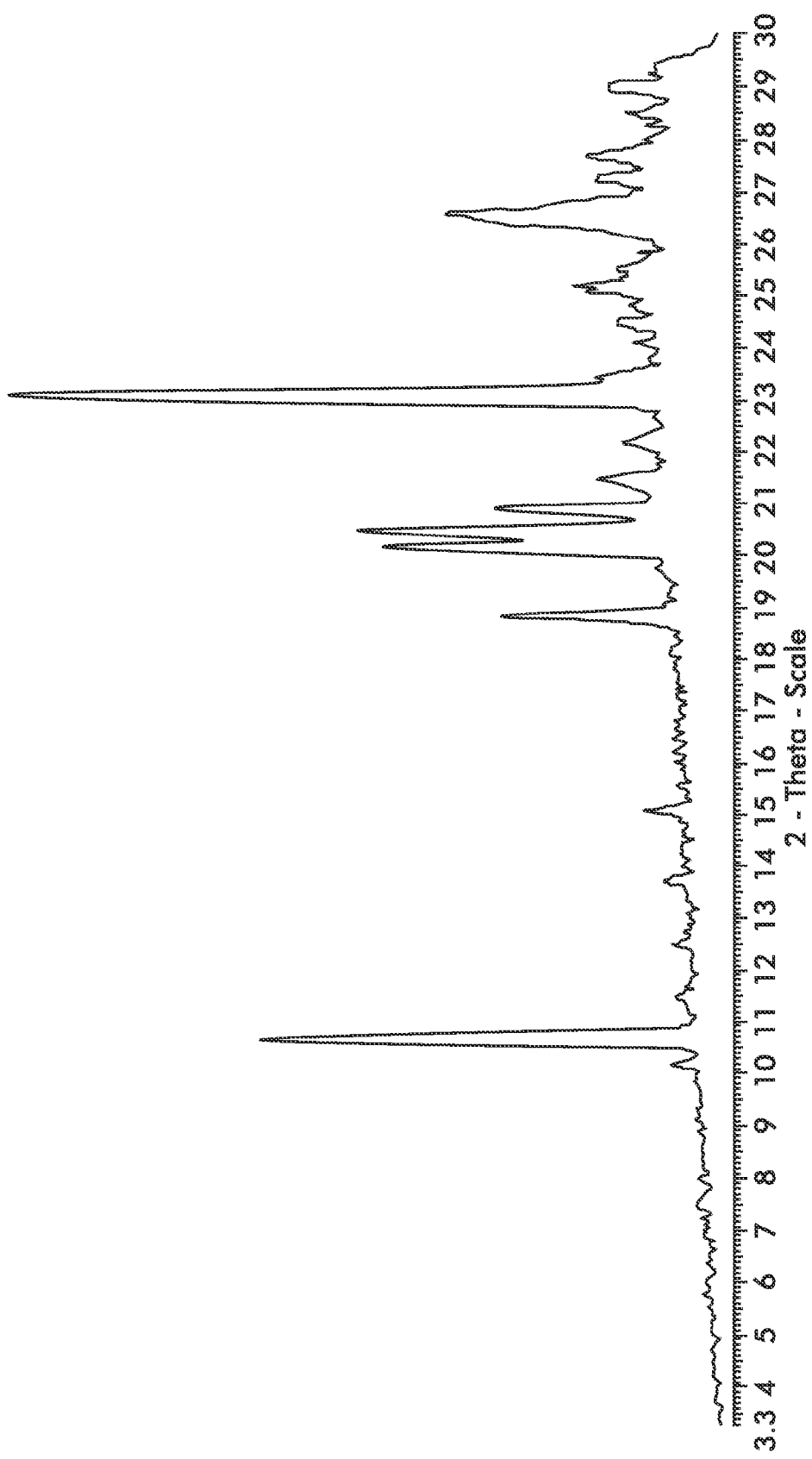
FIG. 6 is an X-ray Powder Diffractogram of bendamustine hydrochloride Form 2
Figure 7A:
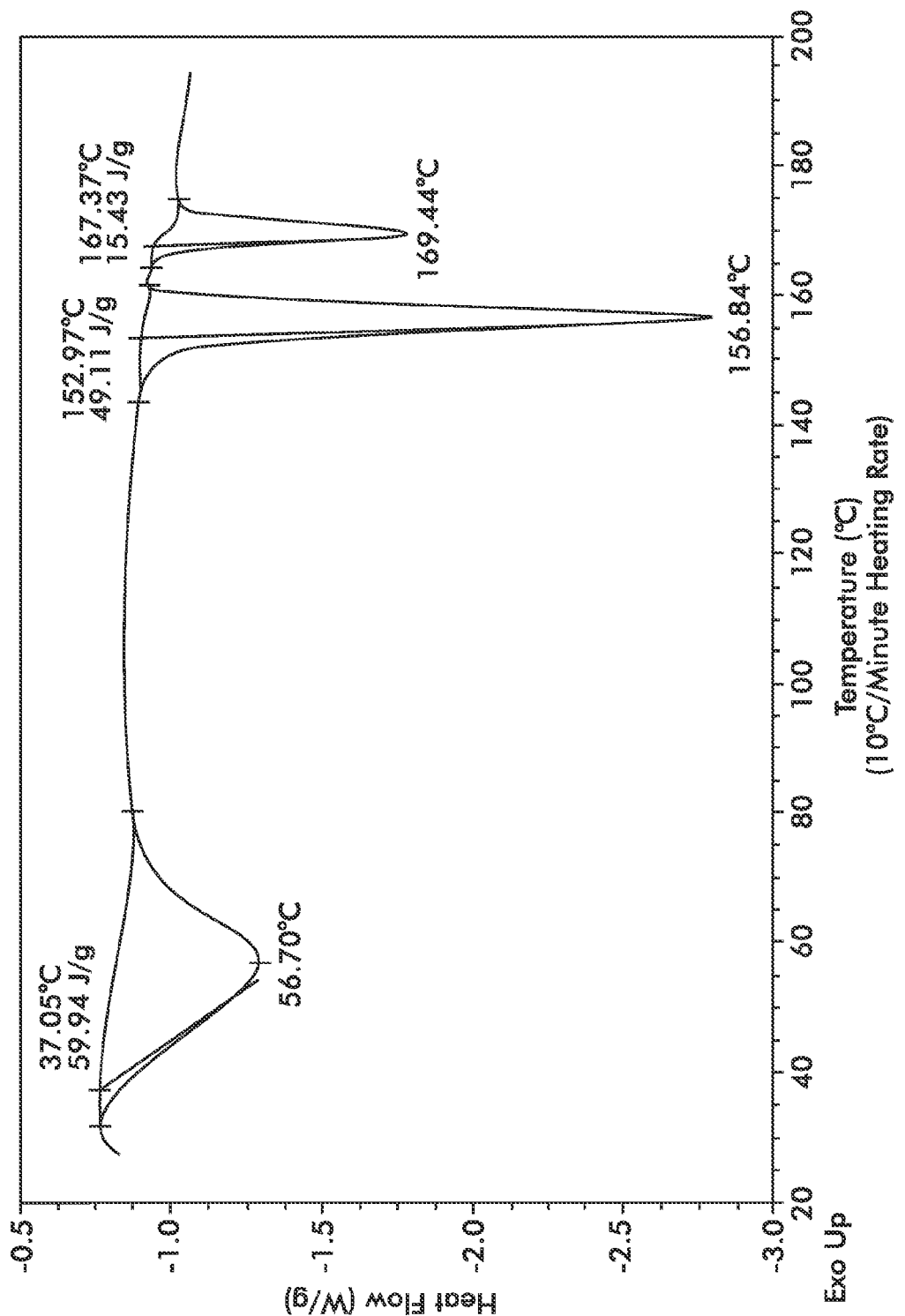
FIG. 7A is a DSC Thermogram of bendamustine hydrochloride Form 2
Figure 7B:
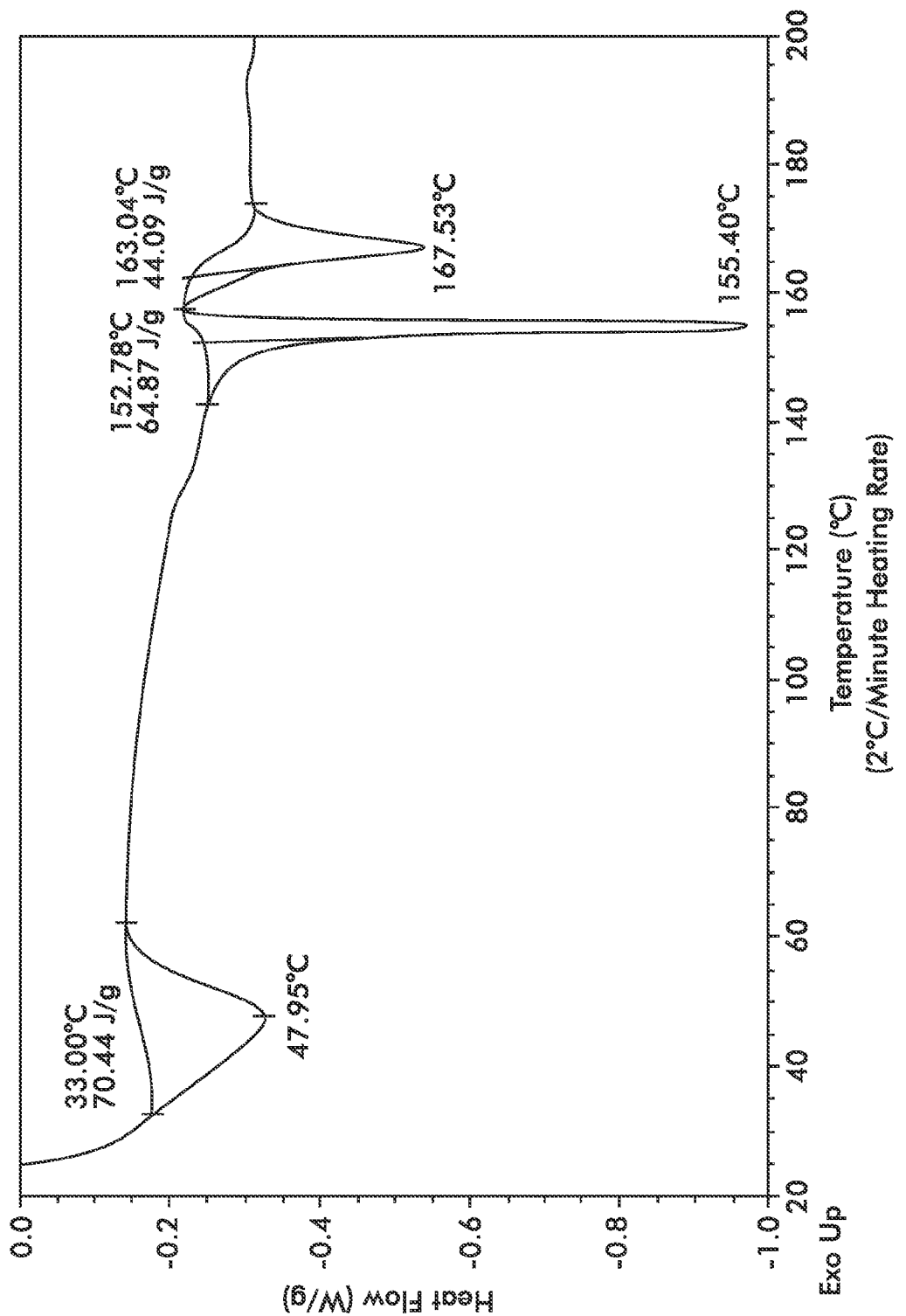
FIG. 7B is a DSC Thermogram of bendamustine hydrochloride Form 2 using a 2° C. per minute heating rate.
Figure 8:
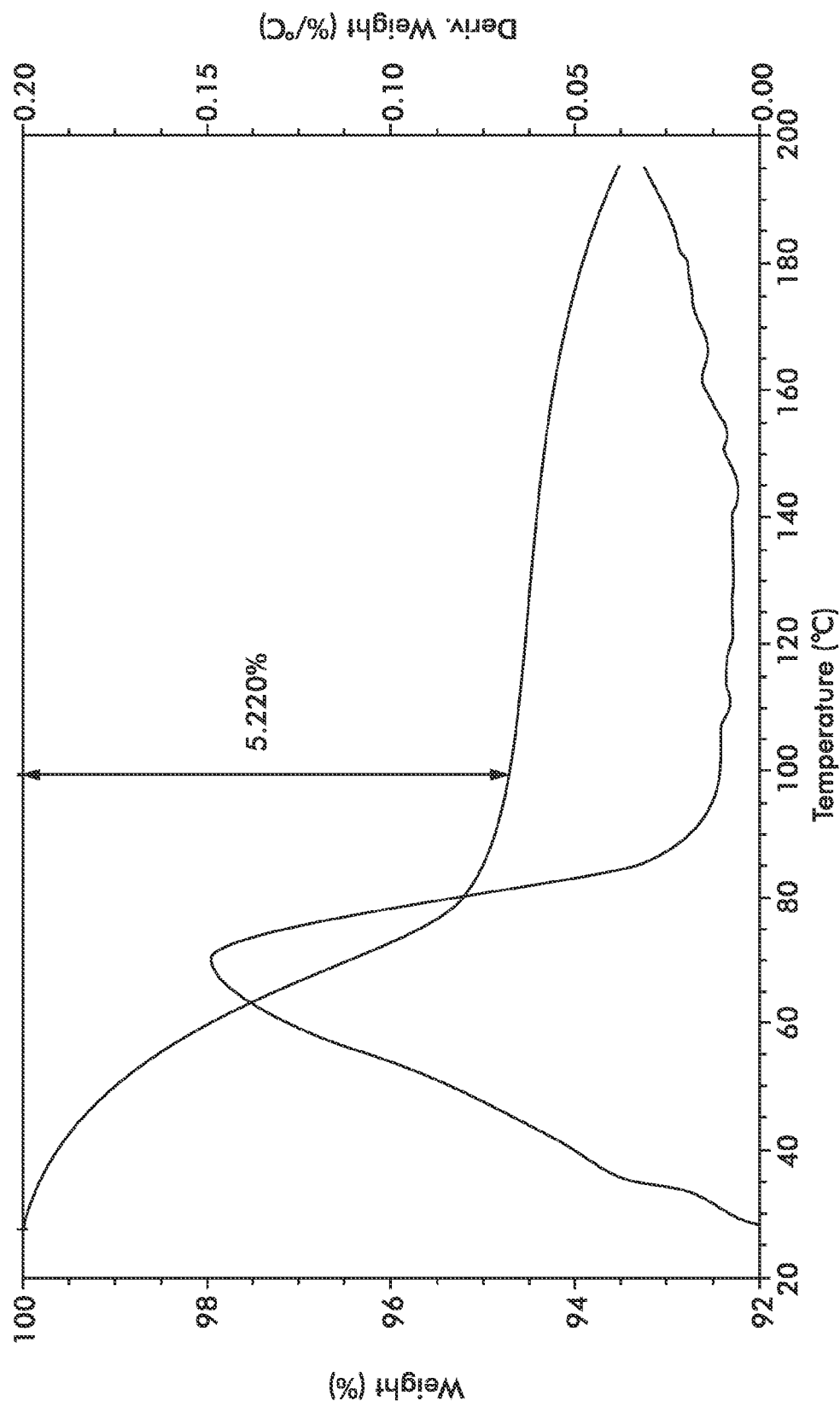
FIG. 8 is a TGA Thermogram of bendamustine hydrochloride Form 2
Figure 9:
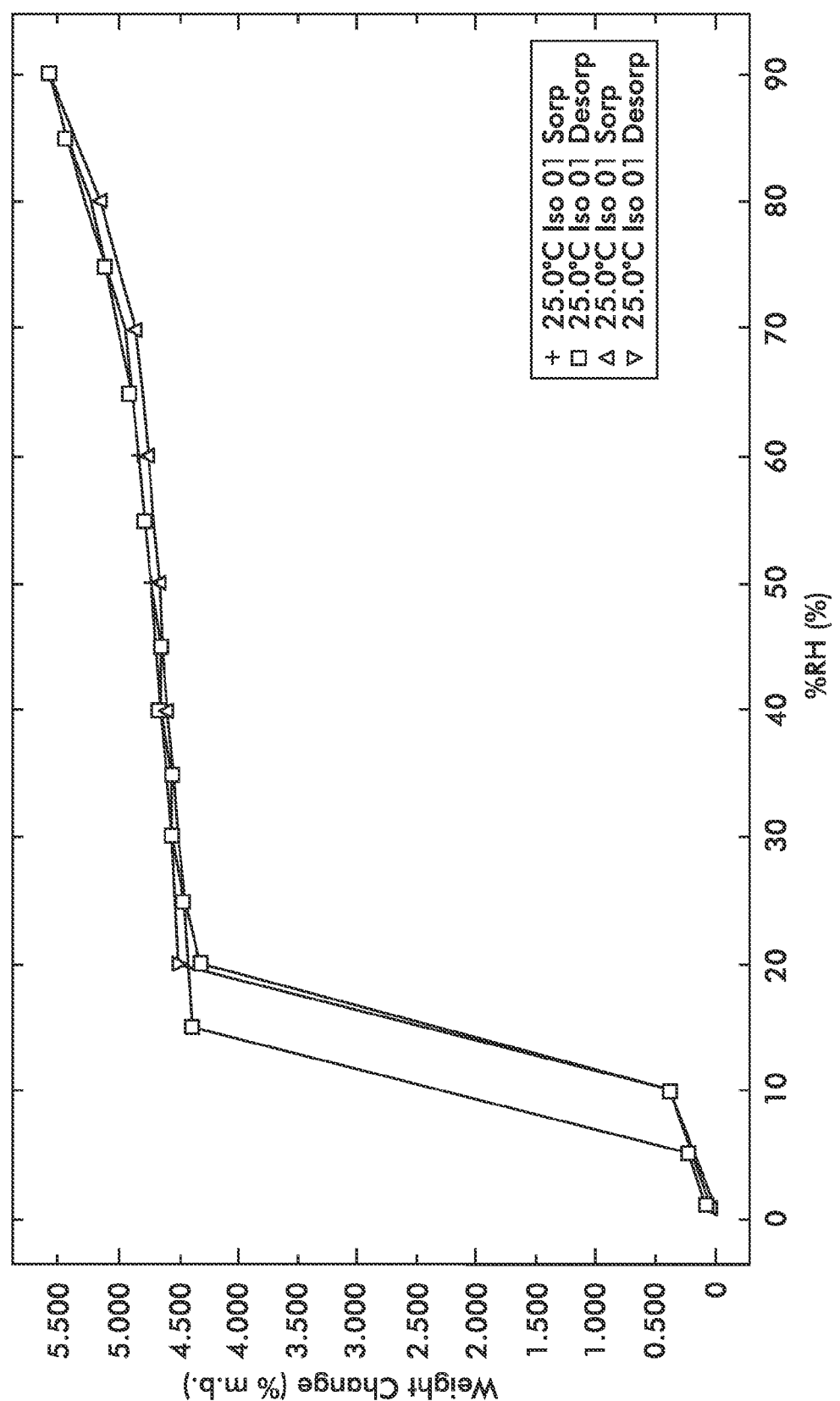
FIG. 9 is a GVS trace of bendamustine hydrochloride Form 2

Other embodiments of the invention are directed to a crystalline form of bendamustine hydrochloride that produces an X-ray powder diffraction pattern comprising one or more of the following reflections: 10.64, 20.12, 20.45, and/or 23.11±0.2 degrees 2θ. The invention is also directed to crystalline forms of bendamustine hydrochloride that produce an X-ray powder diffraction pattern further comprising one or more of the following reflections: 10.17, 15.06, 18.82, 20.95, 25.20, 26.54, and/or 29.05±0.2 degrees 2θ. The invention is also directed to crystalline forms of bendamustine hydrochloride having an X-ray powder diffraction pattern substantially as depicted in FIG. 6. The invention is also directed to pharmaceutical compositions comprising the crystalline form of bendamustine hydrochloride as set forth herein.

Figure 10:
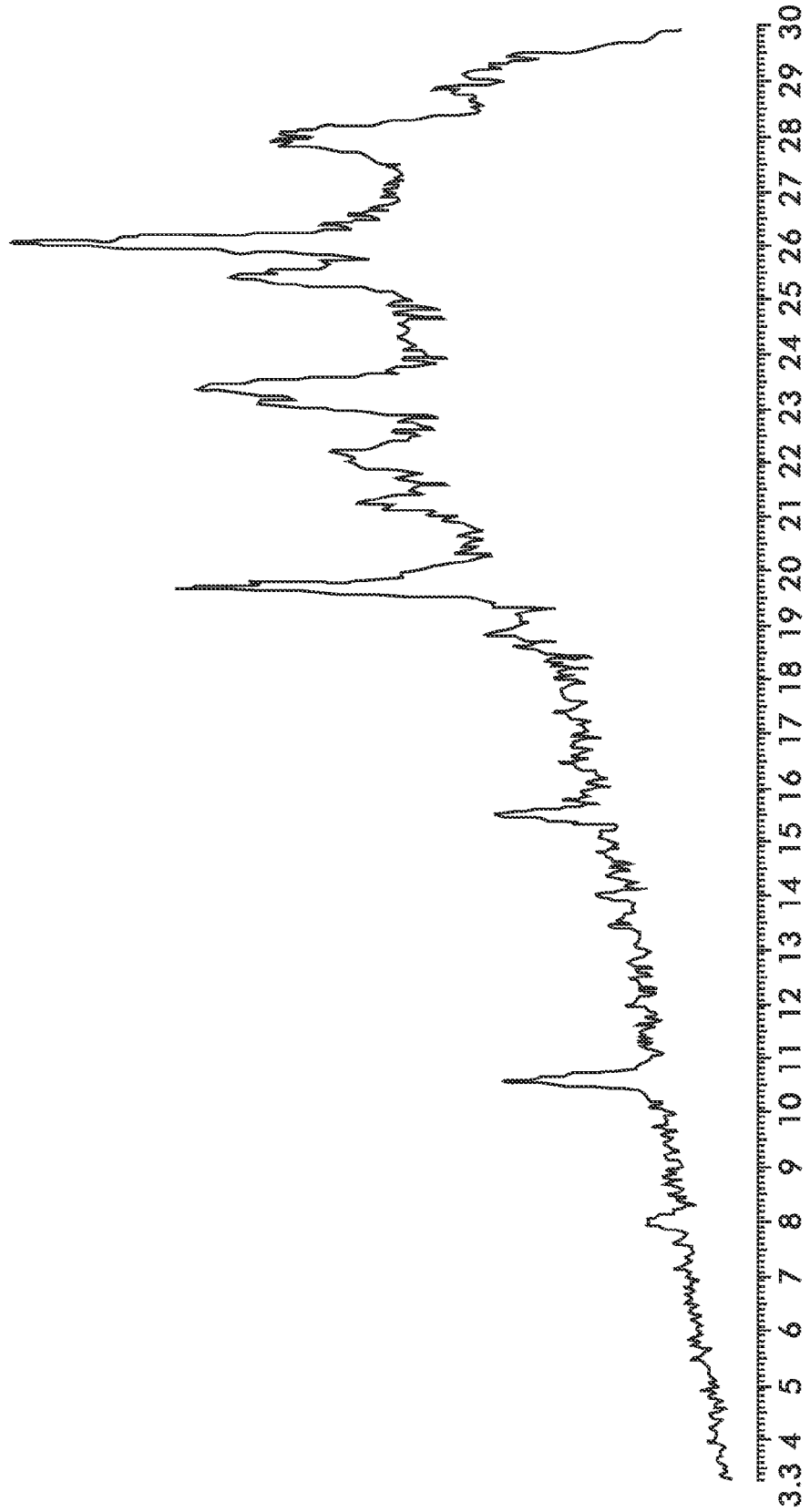
FIG. 10 is an X-ray Powder Diffractogram of bendamustine hydrochloride Form 3

Other embodiments of the invention are directed to a crystalline form of bendamustine hydrochloride that produces an X-ray powder diffraction pattern comprising one or more of the following reflections: 26.08, 27.85, and/or 28.11±0.2 degrees 2θ. The invention is also directed to crystalline forms of bendamustine hydrochloride that produce an X-ray powder diffraction pattern further comprising one or more of the following reflections: 10.58, 15.55, and/or 19.75±0.2 degrees 2θ. The invention is also directed to crystalline forms of bendamustine hydrochloride having an X-ray powder diffraction pattern substantially as depicted in FIG. 10. The invention is also directed to pharmaceutical compositions comprising the crystalline form of bendamustine hydrochloride as set forth herein.

Figure 11:
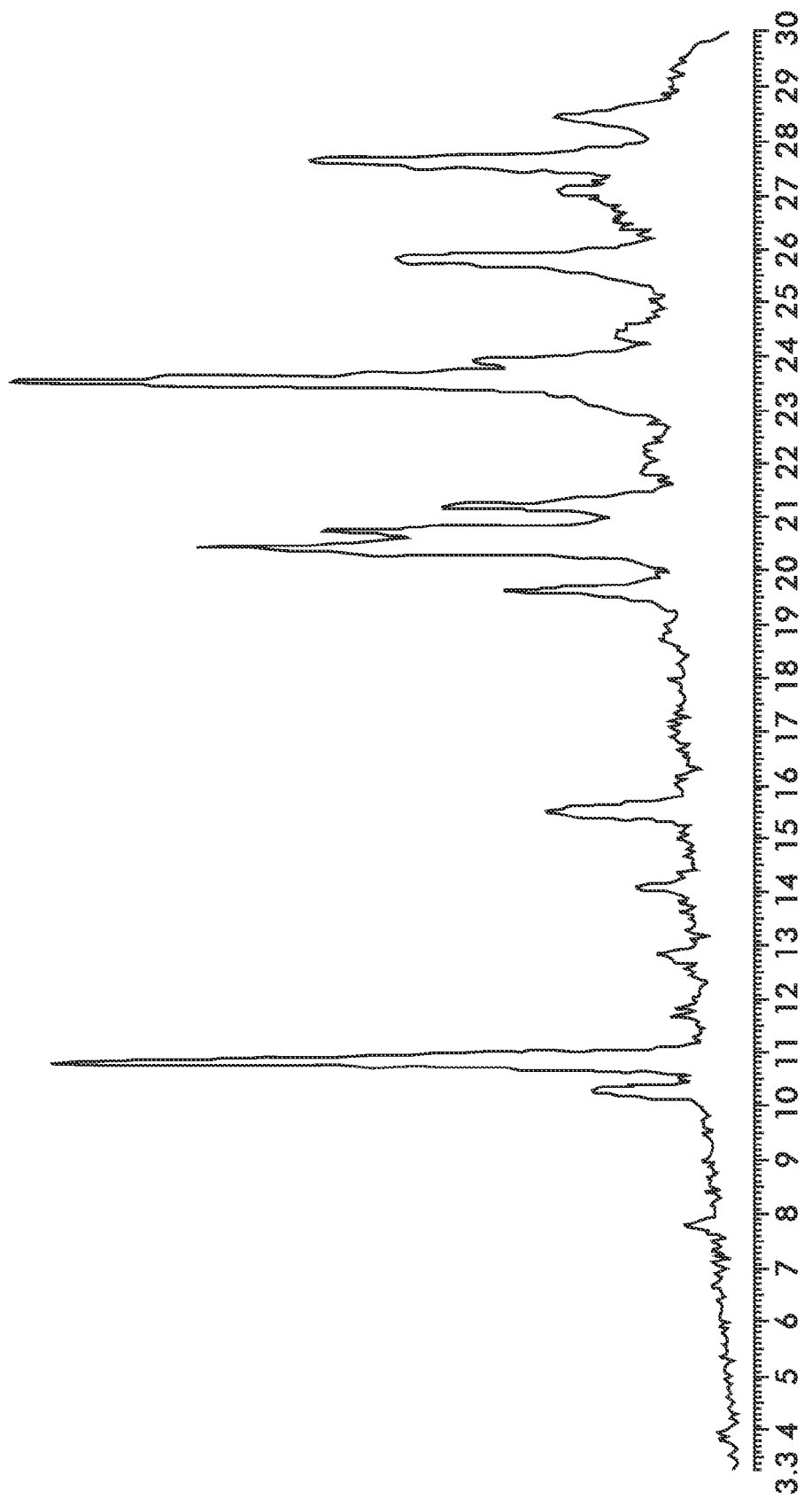
FIG. 11 is an X-ray Powder Diffractogram of bendamustine hydrochloride Form 4
Figure 12:
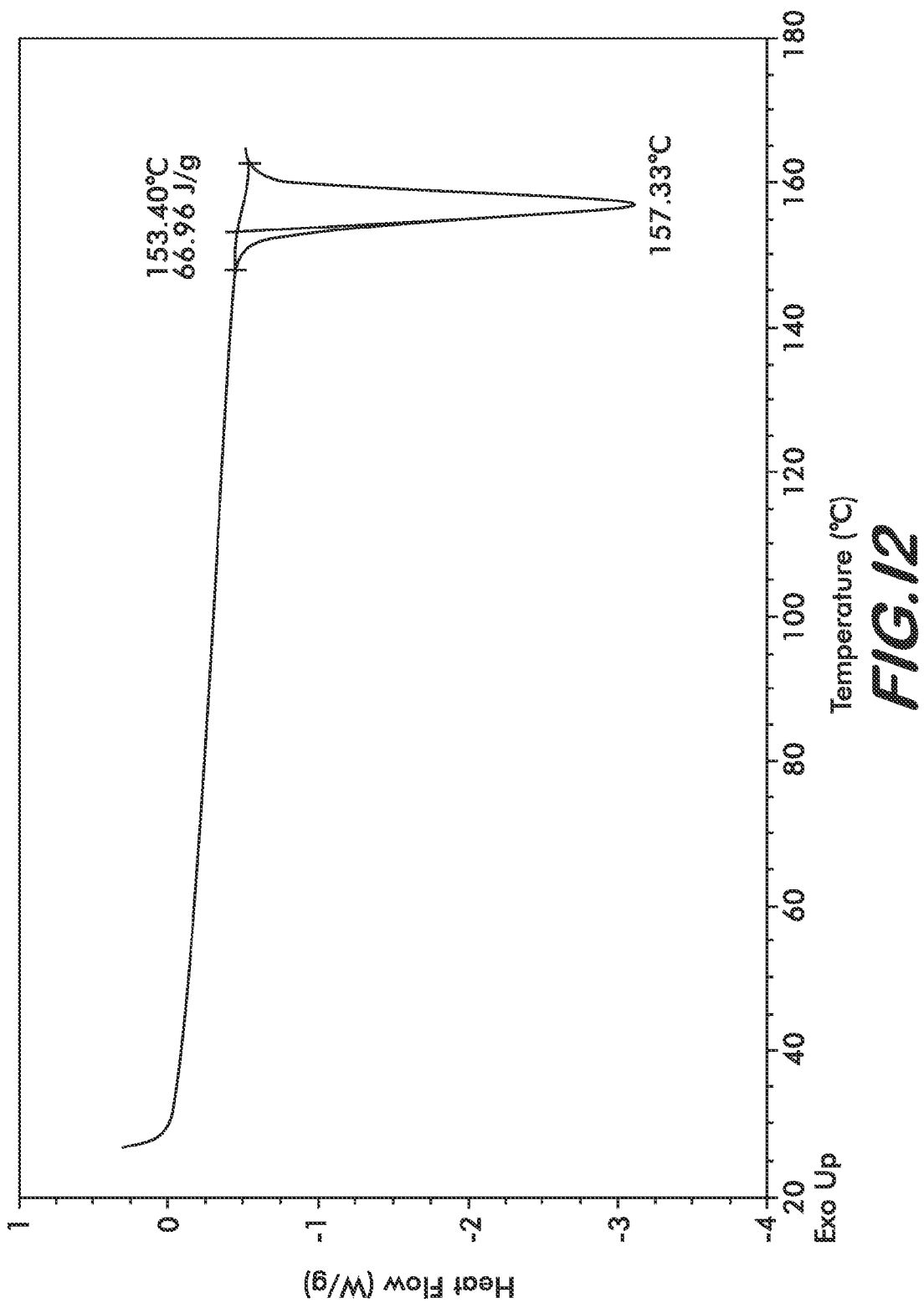
FIG. 12 is a DSC Thermogram of bendamustine hydrochloride Form 4
Figure 13:
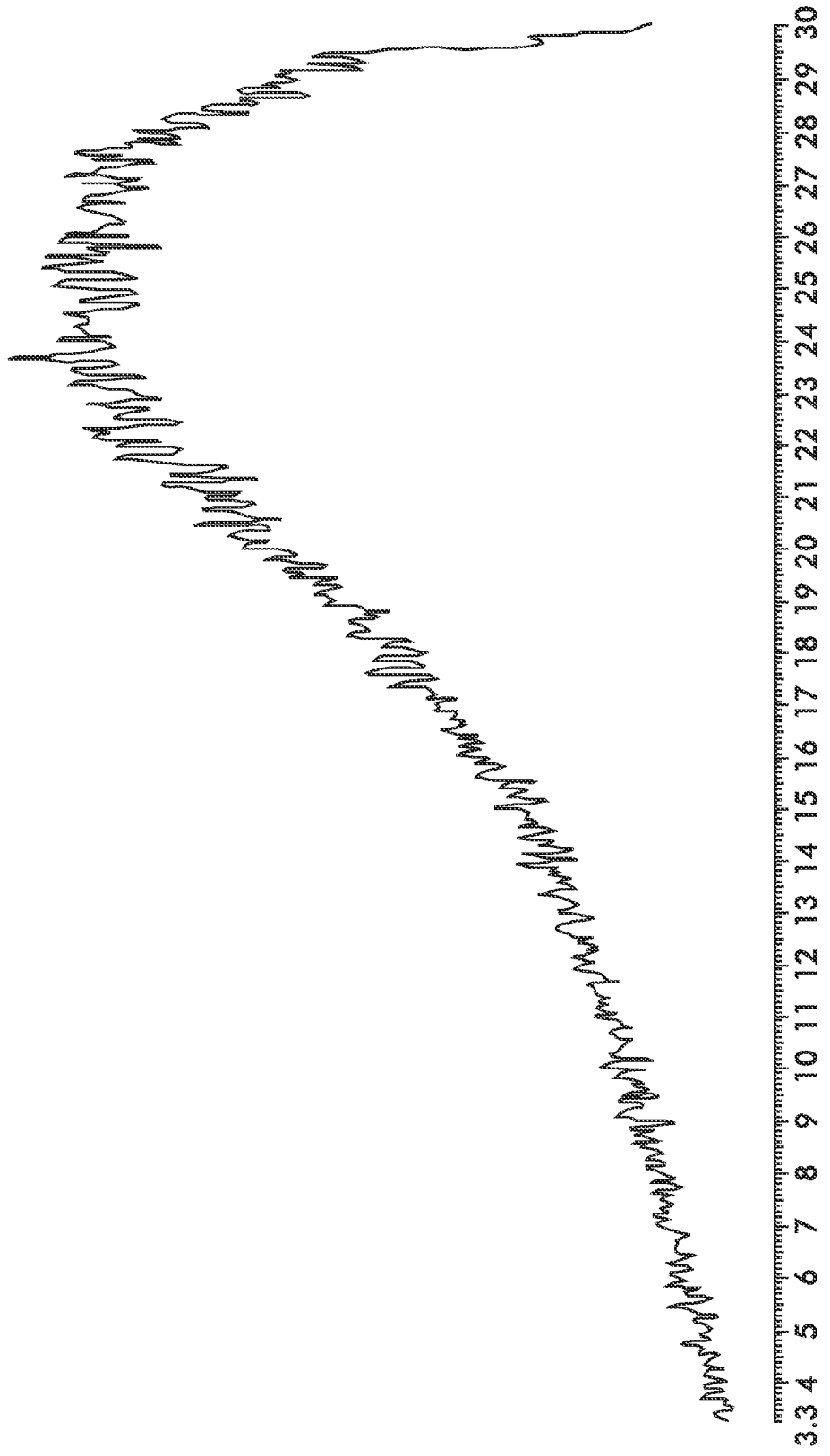
FIG. 13 is an X-ray Powder Diffractogram of amorphous bendamustine hydrochloride

Other embodiments of the invention are directed to a crystalline form of bendamustine hydrochloride that produces an X-ray powder diffraction pattern comprising one or more of the following reflections: 10.83, 15.52, 20.45, and/or 23.58±0.2 degrees 2θ. The invention is also directed to crystalline forms of bendamustine hydrochloride that produce an X-ray powder diffraction pattern further comprising one or more of the following reflections: 10.27, 19.64, 20.73, 21.23, 25.81 and/or 27.63±0.2 degrees 2θ. The invention is also directed to crystalline forms of bendamustine hydrochloride having an X-ray powder diffraction pattern substantially as depicted in FIG. 11. The invention is also directed to pharmaceutical compositions comprising the crystalline form of bendamustine hydrochloride as set forth herein.

Other embodiments of the invention are directed to a lyophilized composition comprising bendamustine hydrochloride Form 1, bendamustine hydrochloride Form 2, bendamustine hydrochloride Form 3, bendamustine hydrochloride Form 4, or a mixture thereof. In certain embodiments, the bendamustine hydrochloride is bendamustine Form 1. In other embodiments, the bendamustine hydrochloride is bendamustine Form 2. In other embodiments, the bendamustine hydrochloride is bendamustine Form 3. In other embodiments, the bendamustine hydrochloride is bendamustine Form 4. The invention is also directed to lyophilized compositions described herein further comprising amorphous bendamustine hydrochloride.

A preferred embodiment of the invention includes a lyophilized composition as described herein, comprising amorphous bendamustine hydrochloride, bendamustine hydrochloride Form 2, and a pharmaceutically acceptable excipient.

Also within the scope of the invention is a method for preparing a lyophilized composition comprising a crystalline form of bendamustine hydrochloride comprising the steps of combining bendamustine hydrochloride with at least one solvent to form a mixture; and lyophilizing the mixture. Preferably, methods of the invention include those wherein the solution further comprises a lyophilization excipient. Preferably, the lyophilization excipient is sodium phosphate, potassium phosphate, citric acid, tartaric acid, gelatin, glycine, mannitol, lactose, sucrose, maltose, glycerin, dextrose, dextran, trehalose, hetastarch, or a mixture thereof. More preferably, the lyophilization excipient is mannitol. Preferably, methods of the invention include those wherein the solvent is water, an organic solvent, or a mixture thereof. Preferably, the organic solvent is methanol, ethanol, n-propanol, iso-propanol, n-butanol, tert-butanol, or a mixture thereof. More preferably, the organic solvent is tert-butanol. In other methods of the invention, the solvent is a mixture of water and an organic solvent. In preferred methods of the invention, the ratio of the water to the organic solvent is about 1:1 (v/v). In preferred methods of the invention, the ratio of the water to the organic solvent is about 2:1 (v/v) In preferred methods of the invention, the ratio of the water to the organic solvent is about 3:1 (v/v) In preferred methods of the invention, the ratio of the water to the organic solvent is about 7:3 (v/v).

In preferred methods of the invention, the crystalline form of bendamustine hydrochloride is Form 1. In other preferred methods of the invention, the crystalline form of bendamustine hydrochloride is Form 2. In still other preferred methods of the invention, the crystalline form of bendamustine hydrochloride is Form 3. In yet other preferred methods of the invention, the crystalline form of bendamustine hydrochloride is Form 4. Other preferred methods of the invention include those wherein the lyophilized composition further comprises amorphous bendamustine hydrochloride.

Also within the scope of the invention are method of treating chronic lymphocytic leukemia, Hodgkin's disease, non-Hodgkin's lymphoma, multiple myeloma or breast cancer comprising administering to a patient in need thereof a therapeutically effective amount of a preparation prepared from a composition as described herein.

Also within the scope of the invention are methods of preparing Form 1 bendamustine hydrochloride comprising providing a solution of bendamustine hydrochloride in ethanol, ethyl acetate, tert-butyl methyl ether, iso-propyl alcohol, isopropyl acetate, dichloromethane, methyl acetate, acetone, tetrahydrofuran, acetonitrile, heptane, toluene, methanol, dioxane, diethyl ether, anisole, nitromethane, or di-isopropyl ether, and evaporating the solution under ambient conditions.

Also within the scope of the invention are methods of preparing Form 1 bendamustine hydrochloride comprising providing a solution of bendamustine hydrochloride in ethanol, methanol, dimethylformamide, dimethylsulfoxide, or dimethylamine, and rapidly evaporating the solution to dryness under ambient conditions.

Also within the scope of the invention are methods of preparing Form 1 bendamustine hydrochloride comprising providing a solution of bendamustine hydrochloride in ethanol, acetic acid, methanol, or dimethylsulfoxide, and slowly evaporating the solution to dryness under ambient conditions.

Also within the scope of the invention are methods of preparing Form 1 bendamustine hydrochloride comprising providing a solution of bendamustine hydrochloride in acetic acid, formamide, dimethylformamide, dimethylsulfoxide, or dimethylamine, and adding a sufficient quantity of toluene to induce crystallization.

Also within the scope of the invention are methods of preparing Form 2 bendamustine hydrochloride comprising providing a solution of bendamustine hydrochloride in dimethylformamide, methanol, or dimethylamine and evaporating the solution under ambient conditions.

Also within the scope of the invention are methods of preparing Form 2 bendamustine hydrochloride comprising providing a solution of bendamustine hydrochloride in acetic acid or methanol, and rapidly evaporating the solution to dryness under ambient conditions.

Also within the scope of the invention are methods of preparing Form 2 bendamustine hydrochloride comprising providing a solution of bendamustine hydrochloride in methanol and slowly evaporating the solution to dryness under ambient conditions.

Also within the scope of the invention are methods of preparing Form 2 bendamustine hydrochloride comprising providing an amount of Form 1 bendamustine hydrochloride and storing the amount at a relative humidity of at least about 88% for a period of time sufficient to convert Form 1 to Form 2.

Also within the scope of the invention are methods of preparing Form 2 bendamustine hydrochloride comprising combining bendamustine hydrochloride Form 1 with water to form a solution and allowing Form 2 to precipitate from the solution.

Also within the scope of the invention are methods of preparing Form 3 bendamustine hydrochloride comprising providing an amount of amorphous bendamustine hydrochloride and storing the amount at about 40° C. and about 75% relative humidity for a period of time sufficient to convert amorphous bendamustine hydrochloride to Form 3.

Also within the scope of the invention are methods of preparing Form 4 bendamustine hydrochloride comprising providing an amount of Form 2 bendamustine hydrochloride and heating Form 2 to about 100° C. for a period of time sufficient to convert Form 2 to Form 4.

Also within the scope of the invention are methods of preparing a pharmaceutical composition of bendamustine hydrochloride comprising the steps of:
preparing bendamustine hydrochloride Form 1; and combining the Form 1 with a pharmaceutically acceptable excipient.

Also within the scope of the invention are methods of preparing a pharmaceutical composition of bendamustine hydrochloride comprising the steps of:
preparing bendamustine hydrochloride Form 2; and combining the Form 2 with a pharmaceutically acceptable excipient.

Also within the scope of the invention are methods of preparing a pharmaceutical composition of bendamustine hydrochloride comprising the steps of:
preparing bendamustine hydrochloride Form 3; and combining the Form 3 with a pharmaceutically acceptable excipient Also within the scope of the invention are methods of preparing a pharmaceutical composition of bendamustine hydrochloride comprising the steps of:
preparing bendamustine hydrochloride Form 4; and combining the Form 4 with a pharmaceutically acceptable excipient Also within the scope of the invention are methods of preparing a lyophilized composition of bendamustine hydrochloride comprising the steps of combining Form 1 bendamustine hydrochloride with a solvent to form a mixture; and lyophilizing the mixture. According to the invention, the Form 1 bendamustine hydrochloride is prepared according to any of the methods described herein.

Also within the scope of the invention are methods of preparing a lyophilized composition of bendamustine hydrochloride comprising the steps of combining Form 2 bendamustine hydrochloride a solvent to form a mixture; and lyophilizing the mixture. According to the invention, the Form 1 bendamustine hydrochloride is prepared according to any of the methods described herein.

Also within the scope of the invention are methods of preparing a lyophilized composition of bendamustine hydrochloride comprising the steps of combining Form 3 bendamustine hydrochloride with a solvent to form a mixture; and lyophilizing the mixture. In certain methods of the invention, the Form 3 bendamustine hydrochloride is prepared by providing an amount of amorphous bendamustine hydrochloride and storing the amount at about 40° C. and about 75% relative humidity for a period of time sufficient to convert amorphous bendamustine hydrochloride to Form 3.

Also within the scope of the invention are methods of preparing a lyophilized composition of bendamustine hydrochloride comprising the steps of: combining Form 4 bendamustine hydrochloride with a solvent to form a mixture; and lyophilizing the mixture. In certain methods of the invention, the Form 4 bendamustine hydrochloride is prepared by providing an amount of Form 2 bendamustine hydrochloride and heating Form 2 to about 100° C. for a period of time sufficient to convert Form 2 to Form 4.

Also within the scope of the invention are lyophilized compositions comprising amorphous bendamustine hydrochloride, wherein said composition is substantially free of any crystalline bendamustine hydrochloride.

In preferred methods of preparing a lyophilized composition of bendmustine hydrochloride, the described mixtures further comprise a lyophilization excipient. Preferably, the lyophilization excipient is sodium phosphate, potassium phosphate, citric acid, tartaric acid, gelatin, glycine, mannitol, lactose, sucrose, maltose, glycerin, dextrose, dextran, trehalose, hetastarch, or a mixture thereof. In more preferred methods, the lyophilization excipient is mannitol.

In preferred methods of preparing a lyophilized composition of bendmustine hydrochloride, the solvent is water, an organic solvent, or a mixture thereof. Preferably, the organic solvent is methanol, ethanol, n-propanol, iso-propanol, n-butanol, tert-butanol, or a mixture thereof. In more preferred methods, the organic solvent is tert-butanol.

In preferred methods of preparing a lyophilized composition of bendmustine hydrochloride, the solvent is a mixture of water and an organic solvent. Preferably, the ratio of the water to the organic solvent is about 1:1 (v/v). Also preferred are those methods wherein the ratio of the water to the organic solvent is about 2:1 (v/v). In other preferred methods, the ratio of the water to the organic solvent is about 3:1 (v/v). In other preferred methods, the ratio of the water to the organic solvent is about 7:3 (v/v).

As those skilled in the art will appreciate, numerous modifications and variations of the present invention are possible in view of the above teachings. It is therefore understood that within the scope of the appended claims, the invention can be practiced otherwise than as specifically described herein, and the scope of the invention is intended to encompass all such variations.

What is claimed:

1. A method of treating chronic lymphocytic leukemia, Hodgkin's disease, non-Hodgkin's lymphoma, multiple myeloma, or breast cancer in a patient in need thereof comprising
administering to the patient a solution prepared from a lyophilized composition comprising a crystalline form of bendamustine hydrochloride that is bendamustine hydrochloride Form 3 that produces an X-ray powder diffraction pattern comprising the following reflections: 7.9, 15.5, and 26.1±0.2 degrees 2θ.

2. The method according to claim 1, wherein the non-Hodgkin's lymphoma is indolent B-cell non-Hodgkin's lymphoma.

3. The method of according to claim 1, for treating chronic lymphocytic leukemia.

4. The method according to claim 1, wherein the bendamustine hydrochloride Form 3 produces an X-ray powder diffraction pattern further comprising one or more of the following reflections: 10.6, 19.7 and/or 23.3±0.2 degrees 2θ.

5. The method according to claim 1, wherein the lyophilized composition is substantially free of other crystalline forms of bendamustine hydrochloride.

6. The method according to claim 1, wherein the lyophilized composition further comprises amorphous bendamustine hydrochloride.

7. The method according to claim 1, wherein the lyophilized composition further comprises at least one pharmaceutically acceptable excipient.

8. The method according to claim 7, wherein the excipient is sodium phosphate, potassium phosphate, citric acid, tartaric acid, gelatin, glycine, mannitol, lactose, sucrose, maltose, glycerin, dextrose, dextran, trehalose, hetastarch, or a mixture thereof.

9. The method according to claim 8, wherein the excipient is mannitol.

10. The method according to claim 1, wherein the lyophilized composition further comprises an organic solvent.

11. The method according to claim 10, wherein the solvent is methanol, ethanol, n-propanol, iso-propanol, n-butanol, tert-butanol, or mixtures thereof.

12. The method according to claim 11, wherein the solvent is tert-butanol.

13. A method for preparing a crystalline form of bendamustine hydrochloride that is bendamustine hydrochloride Form 3 that produces an X-ray powder diffraction pattern comprising the following reflections: 7.9, 15.5, and 26.1±0.2 degrees 2θ comprising
combining bendamustine hydrochloride, mannitol, water, and an organic solvent to form a solution; and
lyophilizing the solution to form the bendamustine hydrochloride Form 3.

14. The method according to claim 13, wherein the bendamustine hydrochloride Form 3 produces an X-ray powder diffraction pattern further comprising one or more of the following reflections: 10.6, 19.7 and/or 23.3±0.2 degrees 2θ.

15. The method according to claim 13, wherein the solvent is methanol, ethanol, n-propanol, iso-propanol, n-butanol, tert-butanol, or mixtures thereof.

16. The method according to claim 13, wherein the solvent is tert-butanol.

17. The method according to claim 13, wherein the lyophilization step comprises the following lyophilization cycle:

| Process parameters | Target Setpoint |
| --- | --- |
| Loading temperature | 5° C. |
| Freezing temperature | Hold at −50° C. for 4 hours |
| Primary drying vacuum | 150 microns |
| Primary drying temperature | Hold at −15° C. for 27 hours |
| Intermediate drying temperature | Hold at −12° C. for 7 hours |
| Secondary drying vacuum | 50 microns |
| Secondary drying temperature | Hold at 40° C. for 15 hours. |

18. The method according to claim 13, wherein the ratio of bendamustine hydrochloride to mannitol is 15:25.5.

19. A lyophilized composition comprising bendamustine hydrochloride prepared according to the method of claim 13.

20. A method of treating chronic lymphocytic leukemia, Hodgkin's disease, non-Hodgkin's lymphoma, multiple myeloma or breast cancer in a patient in need thereof comprising administering to the patient an injectable preparation prepared from the lyophilized composition of claim 19.

21. The method according to claim 20, wherein the non-Hodgkin's lymphoma is indolent B-cell non-Hodgkin's lymphoma.

22. The method of according to claim 20, for treating chronic lymphocytic leukemia.

* * * * *